(12) United States Patent
Gebhard et al.

(10) Patent No.: US 10,533,800 B2
(45) Date of Patent: Jan. 14, 2020

(54) LIQUID FEEDING DEVICE FOR THE GENERATION OF DROPLETS

(71) Applicant: Sanofi Pasteur SA, Lyons (FR)

(72) Inventors: Thomas Gebhard, Kandern (DE);
Roland Kaiser, Efringen-Kirchen (DE);
Bernhard Luy, Freiburg (DE);
Matthias Plitzko, Neuenburg (DE);
Manfred Struschka, Auggen (DE);
Christian Zerillo, Binzen (DE)

(73) Assignee: Sanofi Pasteur SA, Lyons (FR)

( * ) Notice: Subject to any disclaimer, the term of this patent is extended or adjusted under 35 U.S.C. 154(b) by 0 days.

(21) Appl. No.: 15/328,068

(22) PCT Filed: Jul. 20, 2015

(86) PCT No.: PCT/EP2015/066583
§ 371 (c)(1),
(2) Date: Jan. 23, 2017

(87) PCT Pub. No.: WO2016/012414
PCT Pub. Date: Jan. 28, 2016

(65) Prior Publication Data
US 2017/0219283 A1    Aug. 3, 2017

(30) Foreign Application Priority Data

Jul. 21, 2014    (EP) .................................... 14002529

(51) Int. Cl.
*F26B 5/06* (2006.01)
*B01J 2/04* (2006.01)
(Continued)

(52) U.S. Cl.
CPC ................ *F26B 5/065* (2013.01); *A61K 9/19* (2013.01); *A61K 39/00* (2013.01); *B01J 2/04* (2013.01); *B01J 2/18* (2013.01)

(58) Field of Classification Search
CPC . F26B 5/065; A61K 9/19; A61K 39/00; B01J 2/18; B01J 2/04
See application file for complete search history.

(56) References Cited

U.S. PATENT DOCUMENTS 3,601,901 A    8/1971    Rader
4,376,944 A *  3/1983    Reitberger ................. B41J 2/09
                                                    347/47
(Continued)

FOREIGN PATENT DOCUMENTS

CN    1820953    8/2006
CN    101896351    11/2010
(Continued)

*Primary Examiner* — Jessica Yuen

(57) ABSTRACT

The present invention provides, inter alia, for a liquid feeding device for the generation of droplets, in particular for the use in a process line for the production of freeze-dried particles, with a droplet ejection section for ejecting liquid droplets in an ejection direction, the droplet ejection section comprising at least one inlet port for receiving a liquid to be ejected, a liquid chamber for retaining the liquid, and a nozzle for ejecting the liquid from the liquid chamber to form droplets, wherein the liquid chamber is restricted by a membrane on one side thereof, the membrane being vibratable by an excitation unit, wherein the longitudinal axis of the liquid chamber is tilted relative to the longitudinal axis of the nozzle, and/or the liquid feeding device further comprises a deflection section for separating the droplets from each other by means of at least one gas jet, wherein the deflection section gas jet intersects perpendicular with an ejection path of the liquid ejected from the liquid chamber.

40 Claims, 9 Drawing Sheets

(51) Int. Cl.
 *B01J 2/18* (2006.01)
 *A61K 9/19* (2006.01)
 *A61K 39/00* (2006.01)

(56) References Cited

U.S. PATENT DOCUMENTS

| | | | |
|---|---|---|---|
| 5,828,394 A * | 10/1998 | Khuri-Yakub | B05B 17/0607 347/72 |
| 6,095,889 A * | 8/2000 | Demarinis | A63H 5/00 239/211 |
| 6,458,296 B1 | 10/2002 | Heinzen et al. | |
| 6,863,385 B2 * | 3/2005 | Jeanmarie | B41J 2/03 347/77 |
| 7,344,720 B2 | 3/2008 | Haensler | |
| 2006/0012626 A1 * | 1/2006 | Nlend | B41J 2/17546 347/19 |
| 2006/0017782 A1 * | 1/2006 | Nishi | B05B 5/0255 347/55 |
| 2006/0165717 A1 | 7/2006 | Dalencon et al. | |
| 2006/0181583 A1 * | 8/2006 | Usuda | B41J 2/175 347/85 |
| 2008/0060213 A1 * | 3/2008 | Gehrmann | F26B 5/065 34/284 |
| 2009/0035579 A1 | 2/2009 | Coufal et al. | |
| 2011/0050812 A1 | 3/2011 | Boot et al. | |
| 2014/0091155 A1 * | 4/2014 | Jordan | B05B 17/0607 239/4 |

FOREIGN PATENT DOCUMENTS

| | | | |
|---|---|---|---|
| CN | 101959527 | 1/2011 | |
| EP | 1550556 | 7/2005 | |
| EP | 1800745 | 6/2007 | |
| EP | 2101131 A1 * | 9/2009 | F26B 5/065 |
| EP | 2578974 | 4/2013 | |
| JP | 2007319383 A * | 12/2007 | |
| WO | WO 2005/105253 | 11/2005 | |
| WO | WO 2007/006939 | 1/2007 | |
| WO | WO 2008/009309 | 1/2008 | |
| WO | WO 2009/109550 | 9/2009 | |

* cited by examiner

LIQUID FEEDING DEVICE FOR THE GENERATION OF DROPLETS

RELATED APPLICATIONS

This application is a National Phase of PCT Patent Application No. PCT/EP2015/066583 having International filing date of Jul. 20, 2015, which claims the benefit of priority of European Patent Application No. 14002529.7 filed on Jul. 21, 2014. The contents of the above applications are all incorporated by reference as if fully set forth herein in their entirety.

FIELD AND BACKGROUND OF THE INVENTION

The invention relates to the generation of droplets, in particular to be used for the production of freeze-dried pellets as bulkware, wherein a liquid feeding device is applied for the generation of droplets for the production of freeze-dried particles by means of a respective process line for droplet generation and freeze congealing of liquid droplets to form pellets.

The production method generally referred to as freeze-drying, also known as lyophilization, is a process for drying high-quality products such as, for example, pharmaceuticals, biotechnology materials such as proteins, enzymes, microorganisms, and in general any thermo- and/or hydrolysis-sensitive material. With freeze-drying, the frozen product is usually dried via the sublimation of ice crystals into water vapor, i.e. via the direct transition of water content from the solid phase into the gas phase. Freeze-drying is often performed under vacuum conditions but works generally also under atmospheric pressure.

Application examples for freeze-drying processes in the pharmaceutical area comprise drying drugs or APIs (Active Pharmaceutical Ingredients), API formulations, hormones, peptide-based hormones, monoclonal antibodies, blood plasma products or derivatives, vaccines or other injectables and in general substances which otherwise would not be stable over a required time span. Removing the water prior to sealing the product in vials or other appropriate containers for preserving sterility results in that the product can be stored and shipped, and permits that the product can later be reconstituted by dissolving the product in an appropriate medium, such as water or the like, prior to administration, e.g., by intradermal or intramuscular injection.

Design principles for freeze-dryer devices are well-known in the present technical field. For example, tray-based freeze-dryers comprise one or more trays or shelves within a (vacuum) drying chamber. Vials can be filled with the product and arranged on a tray, and then the tray with the filled vials is introduced into the freeze-dryer and the drying process is started.

Process systems combining spray-freezing and freeze-drying are also well-known in the present technical field. For instance, U.S. Pat. No. 3,601,901 describes a highly integrated device comprising a vacuum chamber with a freezing compartment and a drying compartment. The freezing compartment comprises a spray nozzle on top of an upwardly projecting portion of the vacuum chamber. The sprayed liquid is atomized and rapidly frozen into a number of small frozen particles which fall downwardly within the freezing compartment to arrive at a conveyor assembly. The conveyor advances the particles progressively for freeze-drying in the drying compartment. When the particles reach a discharge end of the conveyer, they are in freeze-dried form and fall downwardly into a discharge hopper.

As another example, WO 2005/105253 describes a freeze-drying apparatus for fruit juice, pharmaceuticals, nutraceuticals, tea, and coffee. A liquid substance is atomized through a high-pressure nozzle into a freezing chamber and reduced in temperature to below its eutectic temperature, thereby inducing a phase change of liquids in the liquid substance. A co-current flow of cold air freezes the droplets. The frozen droplets are then pneumatically conveyed by the cold air stream via a vacuum lock into a vacuum drying chamber and are further subjected to an energy source therein to assist sublimation of liquids as the substance is conveyed through the chamber.

Many products to be freeze-dried are compositions comprising two or more different input agents or components which are mixed prior to freeze-drying. Thus, a composition is mixed with a predefined ratio and is then freeze-dried and filled into vials for shipping. A change in the mixing ratio of the composition after filling into the vials is practically not feasible. The mixing, filling and drying processes therefore cannot normally be separated.

WO 2009/109550 A1 discloses a process for stabilizing an adjuvant containing a vaccine composition in dry form. It is proposed to separate if desirable the drying of the antigen from the drying of the adjuvant, followed by blending of the two before the filling or by sequential filling. Specifically, separate micropellets comprising either the antigen or the adjuvant are to be generated. The antigens micropellets and the adjuvants micropellets are then blended before filling into vials, or are directly filled to achieve the desired mixing ratio only at the time of blending or filling. Further it is possible to improve the overall stability, as the stabilizing formulations can be optimized independently for each component. The separated solid states allow to avoid interactions between the different components throughout storage, even at higher temperature.

Products such as to be found in the pharmaceutical or biotechnology area often have to be manufactured under closed conditions, i.e., they have to be manufactured under sterile conditions and/or under containment. Thus, a process line intended for a production under sterile conditions has to be adapted such that no impurities can enter and contaminate the product. Further, a process line adapted for a production under containment has to be adapted such that neither the product, elements thereof, nor auxiliary material can leave the process line and enter the environment. Here, one of the critical components for such a process line, in particular for the sterile manufacture of lyophilized microspheres, is the nozzle device serving to generate droplets to be freeze-dried, sometimes also referred to as spray nozzle or prilling nozzle. In particular, the nozzle can define in a very early stage of the process parameters of the product quality like particle size and particle size distribution. Due to this, the nozzle is a very important component of the bulk freeze drying process and a specific development area due to the number of parts of the nozzle, which are influencing the product quality significantly.

The detailed description of an example of such a prilling nozzle can be found in U.S. Pat. No. 6,458,296 B1, in which a nozzle is provided inside a reactor and consists of a carrier plate with a depression defined by a circular peripheral wall a bore extending from the center point of its bottom. The bore opens in a recess for accommodating a nozzle. Associated with the depression is a pressure ring fixing a diaphragm made of silicone and a seal, such that a pulsation chamber is provided by the diaphragm and the depression.

The diaphragm carries a disk magnet which is fixed to the diaphragm, for example by gluing, and an electrical coil is suspended at a spacing with respect to the disk magnet, wherein alternating current flows passing through the coil generate alternately positive and negative magnetizations. The thus generated magnetic waves act on the disk magnet and cause it to vibrate together with the diaphragm, resulting in a resonant excitation of the same. In the pulsation chamber, a liquid is introduced and urged through the nozzle by the generated vibrations, leaving the nozzle in form of a liquid jet which breaks apart into droplets due to the surface tension, thereby generating ejected droplets, which is known as so called "laminar jet break up". As long as no resonance frequency is initiated, the droplet size distribution is broad. The resonance frequency, however, leads to monosized droplets. Thereafter, the droplets pass through a central aperture of a metal ring connected to a high-voltage source, wherein the ejected droplets penetrate into an electrical field which is built up between the metal ring and the nozzle such that a charge flux occurs in the direction of the nozzle, providing the separated droplets with a similar electrostatic charge causing mutual repulsion of the droplets for separating the droplets from each other.

However, the solution as proposed in U.S. Pat. No. 6,458,296 B1 exhibits certain undesired disadvantages, such as a lack of suitability for CiP ("Cleaning in Place") and/or SiP ("Sterilization in Place") requirements, a weak fixing of the magnet on the diaphragm, leading to easy separation of the magnet, for example caused by heat, a high flexibility of the membrane resulting in the need to stabilize the membrane during sterilization, difficult mounting of the entire structure, a nozzle design intended for sterilization in an autoclave after disassembling the entire structure, no possibility of deaeration, i.e. gas-ventilation, without removing the nozzle, or sticking of the electrostatically charged droplets at the reactor walls or other components inside the reactor, resulting in undesired waste product. Therefore, there is a need for a redesigned prilling nozzle device resolving the cited disadvantages of the known prior art, focusing on improved reproducibility of droplet generation, improved design for CiP and SiP requirements, use of defined GMP ("Good Manufacturing Practice") compatible materials, improved integration of droplet counting, and improved deflection system, i.e. preferably avoiding electrostatic charging that puts an impediment to further particle handling.

As further known prior art in regard to nozzle technique and droplet generation, EP 1 550 556 A1 describes a inkjet recording apparatus for jetting a droplet to a base member, wherein the apparatus comprises in some embodiments a liquid solution supplying section with a liquid solution chamber. Inside the chamber, a piezo element is arranged, and a driving voltage power source is provided for applying a driving voltage for changing the shape of the piezo element in order to achieve the jetting of a droplet to the outside of the chamber through a nozzle.

Now, in order to evaluate if a certain nozzle design provides useable nozzle functionality, droplets need to be identifiable over a distance of preferably 200 mm, wherein a variation of about 500 Hz should still be sufficient to provide droplets over the whole distance but of different droplet size, which indicates the robustness of the droplet formation by the respective nozzle design. The liquid feeding device of the present invention as described below fulfills these requirements.

SUMMARY OF THE INVENTION

In view of the above, the present invention provides a liquid feeding device for the generation of droplets, in particular for the use in a process line for the production of bulkware of freeze-dried particles. In detail, the present invention provides such a liquid feeding device comprising a droplet ejection section for ejecting liquid droplets in an ejection direction, wherein the droplet ejection section comprises at least one inlet port for receiving a liquid to be ejected, also referred to as liquid infeed, a liquid chamber for retaining the liquid, and a nozzle for ejecting the liquid or liquid jet from the liquid chamber to form droplets. Here, the liquid chamber is restricted by a membrane on one side thereof, wherein the membrane is vibratable by an excitation unit. The liquid feeding device can comprise a deflection section for separating the droplets from each other by means of at least one gas jet. Further or alternatively, the liquid chamber can be tilted compared to the horizontal in a way such that the longitudinal axis of the liquid chamber is tilted relative to the longitudinal axis of the nozzle. Moreover, the deflection section gas jet intersects perpendicular with an ejection path of the liquid ejected from the droplet ejection section resulting in separate droplets, also referred to as droplets ejected from the droplet ejection section. With such a structure of the liquid feeding device, the liquid is introduced through the liquid infeed and urged through the liquid chamber and the nozzle by the generated vibrations, leaving the nozzle in form of a liquid jet which breaks apart into droplets due to the surface tension, thereby generating ejected droplets downstream the nozzle. Here, it is to be noted that, in certain embodiments, one may implement a deflection section based on an electrostatic appliance or the like as an addendum or an alternative to the deflection section for separating the droplets from each other by means of a gas jet. Deflection sections based on electrostatic appliance or the like are known in the art. It is to be noted that the ejection direction is to be understood as a direction in which the liquid or liquid jet and, further downstream, the droplets are ejected out of the nozzle, i.e. a direction along or parallel to the longitudinal axis of the nozzle body, and an ejection path is to be understood as the course that the liquid or, further downstream, the droplets travel downstream of the nozzle. In the case that the nozzle is directed vertically downwards towards the ground and the droplets are only affected by gravity, the ejection direction and the ejection path of the droplets coincide, both being directed towards the ground. Now, by means of the at least one gas jet of the deflection section, the droplets can be separated from each other in order to avoid coalescence of the droplets prior to freezing and to improve the heat transfer by spreading the droplets. The gas jet can exit a gas access port provided in the deflection section, wherein the gas used for the gas jet is preferably sterile filtered gas.

In order to achieve the vibrations of the membrane, the excitation unit preferably comprises a combination of a permanent magnet separably attachable to the membrane opposite the liquid chamber and an electromagnetic coil for actuating the permanent magnet. Here, a vertical adjustment of the electromagnetic coil support is necessary to avoid any tilting of the permanent magnet and to ensure a coherent contact to the membrane. A damping element can be provided around the permanent magnet and between the same and the electromagnetic coil for achieving a damping effect between the magnet and the coil, preferably wherein the damping element is made out of silicone, with such molds or shapes of the damping element that the electromagnetic coil and the magnet all have defined positions, and wherein the coil can be made out of copper. The damping element, also referred to as damper, can increase the displacement of the magnet, wherein the damping element preferably accommodates the magnet in a way that it can be just mounted centrically to the electromagnetic coil to avoid any tilting of the magnet. Preferably, medium sized magnets are to be used.

Now, as to the function of the excitation unit, the electrical frequency applied to the electromagnetic coil is transformed into mechanical vibration of the magnet, wherein the applied frequency preferably ranges from 800 Hz to 10,000 Hz, more preferably from 1,300 Hz to 3,500 Hz. The mechanical vibration of the magnet then needs to be transferred further to the membrane, which is in direct contact with the liquid out of which droplets have to be generated. Here, the magnet preferably needs to be in contact with the membrane, for example by means of a magnetic contact or the like. In this regard, it is preferable that the membrane is a stainless steel membrane, i.e. made of the type of stainless steel that has magnetic properties, such as 1.4028 steel or AM 350 steel, preferably GMP compatible, with a preferred thickness of about 100 µm. A stainless steel membrane, for example welded on a flange, provides enough flexibility in order to achieve a precise vibration inside the liquid jet. With the vibrating membrane, a controlled intrinsic vibration can be provided to the liquid jet, such that the liquid jet leaving the nozzle is broken into equally sized droplets by a superimposed mechanical vibration. As an alternative, the mechanical vibration transferred to the membrane may also be generated by other kinds of excitation units, such as units applying a piezo actuator, a mechanical eccentric wheel, or the like. A vertical adjustment of a support of the electromagnetic coil can be advantageous to avoid any tilting of the magnet and to ensure a coherent contact between the magnet and the membrane.

Further, the deflection section can comprise at least one deflection tube for emitting the at least one gas jet, wherein the at least one deflection tube protrudes from a main body of the deflection section in the ejection direction of the droplets. Here, the deflection section comprises a main body and the at least one deflection tube which projects from the main body of the deflection section parallel to the ejection direction of the droplets, i.e. the ejection path of the droplets, such that the deflection tube is basically provided collateral to the droplets ejection path such that the longitudinal axis of the deflection tube and the droplet ejection path are aligned in the same plane. Further, the at least one gas jet emitted from the deflection tube is provided in a manner such that the gas jet is directed towards the droplets, thereby intersecting with the droplet ejection path, preferably perpendicular, i.e. at an angle of about 90°. Moreover, in view of the droplet ejection path, the ejected droplets can pass through a recess provided in the main body of the deflection section in order to arrive in the vicinity of the deflection tube. Here, the recess can be a central through-hole the main body of the deflection section, extending through the same, through which the droplets pass on their way to the intersection point with the gas jet.

Alternatively or additionally, the deflection section comprises at least two deflection tubes arranged opposite to each other. Here, the deflection section comprises a main body and the two deflection tubes project from the main body of the deflection section parallel to the ejection direction of the droplets, i.e. the ejection path of the droplets, such that the deflection tubes are both basically provided collateral, i.e. parallel to the droplets ejection path such that the respective longitudinal axis of the deflection tubes and the droplet ejection path are aligned in the same plane. Further, the at least one gas jet emitted from each of the two deflection tubes is provided in a manner such that the respectively emitted gas jet is directed towards the droplets, thereby intersecting with the droplet ejection path, preferably perpendicular, i.e. at an angle of about 90°.

Due to the arrangement of the two deflection tubes opposite to each other across the droplet ejection path, preferably with the same distance to the droplet ejection path, the emitted gas jets meet each other right at the droplet ejection path of the droplets ejected from the droplet ejection section, thereby intersecting with the same.

Alternatively or additionally, the deflection section comprises four deflection tubes, wherein each two of the four deflection tubes can be arranged opposite to each other. Here again, the deflection section comprises a main body and the four deflection tubes project from the main body of the deflection section parallel to the ejection direction of the droplets, i.e. the ejection path of the droplets, such that the deflection tubes are both basically provided collateral, i.e. parallel to the droplets ejection path such that the respective longitudinal axis of each two of the four deflection tubes arranged opposite to each other and the droplet ejection path are aligned in the same plane. Further, the at least one gas jet emitted from each of the four deflection tubes is provided in a manner such that the respectively emitted gas jet is directed towards the droplets, thereby intersecting with the droplet ejection path, preferably perpendicular, i.e. at an angle of about 90°. Thereby, the at least four gas jets preferably intersect with each other at the droplet ejection path. This allows that the ejected droplets might also enter the deflection section de-centered from the longitudinal or vertical axis, i.e. the droplet ejection path, which makes a droplet deflection function more robust, resulting in that a higher resistance against vertical deviations can be achieved.

Moreover, in view of the droplet ejection path, the ejected droplets can pass through a recess provided in the main body of the deflection section in order to arrive in the vicinity of the deflection tubes. Here, the recess can be a central through-hole of the main body of the deflection section, through which the droplets pass on their way to the intersection point with the gas jets. The central through hole, also referred to as a transition zone for the droplets or pre-deflection zone, can be provided as a straight bore hole in a cylindrical form. However, with a straight transition zone, it becomes possible that turbulences may cause a deposition of droplets in horizontal or vertical areas that accumulate and coalesce into larger droplets, i.e. so called dripping, which deteriorates product quality and yield. Alternatively, the central through-hole can be provided as a conical through-hole, with an increasing diameter in the direction towards the deflection tubes. Here, the opening of the diameter of the conical shape is preferably chosen to avoid any deposition of small droplets, so called satellites, in the pre-deflection zone. After leaving the conical zone, the droplets get separated from each other by deflection gas jets. In the main body of the deflection section, the gas for the gas jets is guided in a chamber inside the main body around the transition zone, from where it is finally transferred into the vertical deflection tubes.

The precision requirements for the deflection gas jets are high since they have to meet exactly in the center between each other where the droplets fall downwards. Thus, since the emitted gas jets from the two deflection tubes being arranged opposite to each other meet exactly at the droplet ejection path, a separation of the droplets from each other is achieved, resulting in a desired distribution of the mono-sized droplets without the risk of droplets interfering with each other, for example by merging into one undesired combined droplet of twice the mass and size. In order to achieve an optimum droplet distribution, each deflection tube comprises at least two gas jet outlet ports in the form of lateral openings in the deflection tubes, preferably three gas jet outlet ports, for example with a diameter of about 0.4 mm.

Furthermore, each deflection tube has an inclined tip end, wherein the gas jet outlet port at the tip of the respective deflection tube, i.e. the lowest deflection opening is positioned in the lowest position and connects with the tube interior at its edge in order to drain the entire deflection tube during CiP and SiP processes. Here again, the precision requirements for the gas jet outlet ports are high since the gas jets have to meet in the center at the droplet ejection path. In general, the deflection by gas uses preferably 0.1 $m^3/h$-0.3 $m^3/h$, further preferably 0.2 $m^3/h$ of deflection gas per outlet port.

In accordance with a further preferred implementation of the present invention, the droplet ejection section comprises at least one outlet port besides the at least one inlet port, the liquid chamber and the nozzle. Preferably, the at least one outlet port, also referred to as liquid outfeed, is arranged at an outer circumference of the liquid chamber, contrary to the at least one inlet port, which is preferably arranged near the center of the liquid chamber in the vicinity of the nozzle. Here, as mentioned above, the longitudinal axis of the liquid chamber can be tilted relative to the longitudinal axis of the nozzle, preferably in a way that the at least one outlet port is provided at the highest level of the liquid chamber, wherein the longitudinal axis of the liquid chamber thus coincides with the ejection direction of the liquid. This means that the liquid chamber which generally has a larger lateral dimension than longitudinal dimension is provided in an inclined manner such that the liquid chamber will be filled by liquid entering from the at least one inlet port until it reaches the at least one outlet port at the higher level or higher position, thereby ensuring that sufficient liquid is provided to the nozzle for ejection. In order to avoid waste of excessive liquid in the liquid chamber by releasing the same through the outlet port or in order to avoid a breach of sterile conditions, a blocking means can be provided subsequently to the outlet port, such as a check valve, a shut-off valve or the like. With the described inclination of the entire liquid chamber, the liquid carrying cavity is self draining and self-venting, i.e. self-deaerating, in order to avoid any gas bubbles that would change the vibration properties. Hereto, it is to be noted that liquids are non compressible, whereas gas bubbles are compressible, therefore the existence of gas bubbles inside the liquid chamber would be highly disadvantageous since the vibration work would be absorbed by the gas bubbles.

The at least one outlet port, which can also be referred in functional term to as a bypass opening, however, can not only serve for drainage of excessive liquid to be ejected from the liquid chamber but can primarily serve for discharge of SiP fluid and/or CiP fluid introduced through the at least one inlet port into the liquid chamber. Here, it is to be noted that the drainage of excessive liquid to be ejected can compromise a sterile application of the liquid feeding device in that an open outlet port might violate sterile conditions of the same. Therefore, a drainage function of the liquid chamber by means of the outlet port might be only relevant or desired when using the liquid feeding device of the invention not under sterile conditions. In regard of the discharge function of SiP fluid and/or CiP fluid, it is noted that, since the cross section of the outlet port is larger than the orifice of the nozzle, it becomes possible to feed a larger amount of SiP fluid or SiP fluid through the liquid chamber and thereby through the droplet ejection section, resulting in a faster and more effective way to clean or sterilize the droplet ejection section (i.e. the at least one inlet port, the liquid chamber, the at least one outlet port and the nozzle) compared to a structure where the nozzle is the only possibility for drainage of any fluid inside the liquid chamber. In other words, the provision of the outlet port allows higher cleaning liquid flows and higher sterilization fluid flows, for example saturated steam flows.

In accordance with the present invention, the droplet ejection section can comprise an actuation portion and a nozzle portion, wherein the actuation portion comprises at least the excitation unit, and wherein the nozzle portion comprises at least the membrane, the at least one inlet port, the liquid chamber and the nozzle. Furthermore, in accordance with above, the nozzle portion can further comprise the at least one outlet port. Moreover, the nozzle portion can comprise a nozzle portion main body and a nozzle body which is provided separately from the nozzle portion main body. In doing so, it is possible to manufacture the nozzle portion main body and the nozzle body separate from each other, i.e. it becomes possible to establish the nozzle channel in the nozzle body separately from the nozzle portion main body, for example by the means of drilling the orifice channel into the nozzle body centrically on a turning lathe or the like. Thereby, high precision requirements of the drilling of the nozzle channel can be achieved, which is necessary for implementing straight droplet ejection jet from the orifice and for preventing a tilted droplet ejection jet. After the drilling of the orifice channel, the nozzle body in the form of an insert can be permanently installed in a central through-hole provided in the nozzle portion main body, wherein the liquid chamber and the outside of the droplet ejection section are connected by the nozzle channel. Here, the installing of the nozzle body insert into the nozzle portion main body can be achieved by laser welding or the like. Thus, a nozzle function with a vertical droplet ejection jet can be achieved by the described two-part system consisting of nozzle body and nozzle portion main body. Here, precise adjustment is necessary to ensure the vertical orifice. The length of the orifice channel is preferably between 0.5 mm to 2.0 mm, more preferably between 0.5 mm to 1.0 mm, and the diameter of the nozzle orifice preferably lies within a range of 100 µm to 1000 µm, further preferably within a range of 120 µm to 600 µm, more preferably about 300 µm. Here, since half of the desired droplet diameter can be assumed as the corresponding nozzle orifice diameter, a desired pellet size of approx. 600 µm should be achieved by an orifice diameter of approx. 300 µm. The deaeration connection as described above avoids that gas bubbles are sticking in the nozzle.

In order to be able to provide an airtight closure of the liquid chamber on the side of the membrane, the same is welded to the nozzle portion of the droplet ejection section, preferably by laser welding or the like. Here, the membrane can also be welded into a separate flange which is provided separately from the nozzle portion in order to be able to disassemble and inspect all the single components. The welding of the membrane is reproducible and will lead to the same displacement even with a different product. In general, in view of the above described structure of the actuation portion comprising the excitation unit with a combination of the permanent magnet separably attachable to the membrane, the electromagnetic coil and the damping element, the mounting of the entire design needs to ensure that all these components are in close contact. In practice, this is achieved by putting all the components in a suspended, higher position and fixating them by means of at least one positioning screw, then loosening the positioning screw and allowing the components to have magnetic contact. By this, a sufficiently defined allocation of forces is achieved. The positioning screw has to be designed such that the forces induced by the screw do not interfere with the strictly vertical alignment of all components, which can be the case in the known prior art.

In accordance with a further preferred implementation of the present invention, the liquid feeding device further comprises a CiP/SiP section being arranged between the droplet ejection section and the deflection section for providing CiP fluid and/or SiP fluid to the parts of the liquid feeding device subsequent to the droplet ejection section. In this section, a lateral access for cleaning liquid and steam is provided. Here again, the section is provided with a central through-hole for allowing the ejected droplets still in the form of a droplet ejection jet to pass through, wherein the droplet ejection jet leaving the nozzle orifice transforms by means of the resonance frequency vibrations from the membrane into separate, discrete liquid sections which take the shape of a perfect sphere due to superficial tension of the ejected liquid. The height of the CiP/SiP section, i.e. the length of the through-hole therein is preferably in the range of 20 mm to 50 mm, more preferably 30 mm to 40 mm. Only after the CiP/SiP section, separate droplets are available.

As to the further structure of the liquid feeding device of the present invention, the liquid feeding device preferably further comprises a droplet counting section for counting the ejected droplets, wherein the droplet counting section can be provided before the deflection section in the ejecting direction of the droplets, i.e. in between the CiP/SiP section and the deflection section. The droplet counting section preferably comprises a droplet counting means, for example an optically counting means, which can be implemented by a glass segment or glass tube and ports for fibre optics or the like, wherein the fibre optics serve for counting of the droplets by means of an optical sender and an optical receiver. In particular, the glass tube can be introduced as a glass cylinder integrated into a flange that carries opening ports to take up a light emitting sender and a respective receiver for registering droplets that pass there in-between. The droplet counting section allows to count each single droplet and, thereby, to evaluate if the counted number corresponds to the estimated ejected droplets generated by the frequency of the vibration of the membrane. If this is the case, it can be determined that the droplet generation is as intended, whereas a deviating result can be taken as a signal for a malfunction, resulting in an alarm or the like.

In general, in view of the above described structure of the liquid feeding device of the present invention, including all the different sections, the mounting of the entire design needs to ensure that all these sections are in vertical alignment, in particular in order to achieve the intersection of the ejected droplets with the deflection gas jets. In practice, this is achieved by different centering means, for example by means of centering bores and respective centering protrusions at the single sections.

According to a further aspect of the invention, a freezing chamber of a process line for the production of freeze-dried particles is provided, preferably for the pharmaceutical field, which freezing chamber comprises a liquid feeding device as described above for the generation of droplets to be fed into the freezing chamber. Further, according to another aspect of the invention, a process line for the production of freeze-dried particles is provided by the present invention, comprising such a freezing chamber.

The above mentioned particles can comprise, for example, pellets and/or granules. The term "pellets" as used herein may be understood as preferably referring to particles with a tendency to be spherical. Pellets with sizes in the micrometer range are called micropellets. Accordingly, micropellets obtained with a nozzle in accordance with the invention may have a substantial spherical shape with an aspect ratio close to 1, preferably ranging from 0.8 to 1. According to one example, the liquid feeding device of the present invention can be used for the production of essentially or predominantly spherical freeze-dried micropellets with a mean value for the diameters thereof chosen from a range of about 200 μm to about 1500 μm, or from about 400 μm to about 1000 μm, and more preferably from about 500 μm to about 800 μm. The micropellets obtained with a nozzle according to the invention have a narrow distribution around a mean value. Preferably, they also have a substantial symmetric or normal distribution around a mean value. The span which represents the narrowness of distribution of particles around a mean value is calculated according to the formula: $(D_{90}-D_{10})/D_{50}$ where $D_{90}$, $D_{10}$ and $D_{50}$ represent, respectively, the diameters of 90% or less, 10% or less, and 50% or less of the particles. The micropellets obtained with a nozzle in accordance with the invention may have a span equal or below about 1, preferably equal or below about 0.8, further preferably equal or below about 0.7, further preferably equal or below about 0.6, further preferably equal or below about 0.4, and even further preferably equal or below about 0.2. According to one embodiment, when using a nozzle in accordance with the invention having a diameter of 300 μm, the span of the obtained particles may be equal or below about 0.8, preferably equal or below about 0.7, and more preferably equal or below about 0.6. The measure of the size of micropellets obtained with a nozzle in accordance with the invention may be made by laser granulometry (or laser-diffraction scattering) using, for example, a Malvern Mastersizer 2000 apparatus. For example, a sample of micropellets (e.g. of a volume of 50 ml) may be prepared under nitrogen flushing. The sampler used may be a SCIROCCO 2000a with a large hopper. The measure is performed using the Fraunhofer method, with a measure of the background noise for 10 seconds, a measuring time of 60 seconds, pressure of 0.8 bar, vibration at 50% and obscuration between 0.5% and 40%.

The term “bulkware” can be broadly understood as referring to a system or plurality of particles which contact each other, i.e., the system comprises multiple particles, microparticles, pellets, and/or micropellets. For example, the term “bulkware” may refer to a loose amount of pellets constituting at least a part of a product flow, such as a batch of a product to be processed in a process device or a process line, wherein the bulkware is loose in the sense that it is not filled in vials, containers, or other recipients for carrying or conveying the particles/pellets within the process device or process line. Similar holds for use of the substantive or adjective “bulk.” The bulkware as referred to herein will normally refer to a quantity of particles (pellets, etc.) exceeding a (secondary, or final) packaging or dose intended for a single patient. Instead, the quantity of bulkware may relate to a primary packaging; for example, a production run may comprise production of bulkware sufficient to fill one or more intermediate bulk containers, so called IBCs.

Flowable materials suitable for the liquid feeding device of the present invention include liquids and/or pastes which, for example, have a viscosity of less than about 300 mP*s. As used herein, the term “flowable materials” is interchangeable with the term “liquids” for the purpose of describing materials being fed by the present liquid feeding device to the subsequent devices or sections. Any material may be suitable for use with the techniques according to the invention in case the material is flowable, and can be atomized and/or prilled. Further, the material must be congealable and/or freezable.

The terms "sterility" or "sterile conditions" and "containment" or "contained conditions" are understood as required by the applicable regulatory requirement for a specific case. For example, "sterility" and/or "containment" may be understood as defined according to GMP requirements.

Embodiments of the liquid feeding device may comprise any device adapted for a droplet generation from a liquid as described above. Freezing can be achieved by gravity falldown of the droplets in a chamber, tower, or tunnel. Exemplary freezing chambers include, but are not limited to prilling chambers or towers, atomization devices such as atomization chambers, nebulization/atomization and freezing equipment, etc.

In particular embodiments, the entire liquid feeding device (or sections thereof) can be adapted for CiP and/or Si P. Access points for introduction of a cleaning medium and/or a sterilization medium, including, but not limited to use of nozzles, steam access points, etc., can be provided throughout the sections of the device. For example, steam access points can be provided for steam-based SiP. In some of these embodiments, all or some of the access points are connected to one cleaning and/or sterilization medium repository/generator. For example, in one variant, all steam access points are connected to one or more steam generator in any combination.

Various embodiments of the present invention provide one or more of the advantages discussed hereafter. For example, with the liquid feeding device as presented herein, it is possible to avoid all disadvantages of the known prior art. In particular, with the liquid feed device of the present invention, it becomes possible to achieve the desired product quality like particle size and particle size distribution in a very early stage of the production process.

Furthermore, with the stainless steel membrane of the presented liquid feeding device, receiving an FDA certificate may be facilitated compared to the known PTFE membranes or the like.

Moreover, mounting of the inner structure of the liquid feeding device is simplified, wherein it becomes possible to remove the magnet without difficulty compared to the known prior art in which the head of the nozzle with fixing of the electromagnetic coil has to be screwed together with the membrane flange and the nozzle body, such that a removal of the magnet during sterilization becomes impossible (heating reduces the permanent magnetic properties). Also, since the magnet as provided in the devices as known from the above cited prior art is glued to the membrane, fixing of the magnet on the membrane is weak such that, during disassembling and cleaning, the magnet it is often separated from the membrane and has to be glued again onto the membrane; also, a separation of the magnet from the membrane is facilitated by hot surfaces, which will be the case during sterilization. The thus heat sensitive magnet, however, needs to be in position all the time.

As a further advantage of the present invention, deaeration of the nozzle is possible with the structure of the liquid feeding device of the present invention, which is necessary for a clear droplet formation.

Also, it has not been possible with the known drilled nozzles of the prior art to achieve straight vertical droplet jets. All known stainless steel nozzle tips directly processed into a stainless steel nozzle main body showed an undesired tilted liquid droplet jet. Only by providing the nozzle body separate from the main body during drilling and fixating the same into the main body afterwards, an improved nozzle channel has been generated which results in an improved straight droplet jet.

Furthermore, with a liquid feeding device as presented herein, in particular by providing the liquid chamber with an outlet port, it becomes possible to achieve sufficient steam throughput for sterilization, and thus, it becomes possible to equip a process line for the production of freeze-dried particles with the possibility to maintain closed conditions at all times, even during sterilization procedures. Therefore, sterile and/or contained product handling is enabled while avoiding the necessity of putting the entire process line into a separator or isolator. In other words, a process line provided with a liquid feeding device according to the invention adapted for example for an operation under sterile conditions can be operated in an unsterile environment. Costs and complexity related to using an isolator can therefore be avoided while still conforming to sterile and/or containment requirements, for example GMP requirements. For example, there may be an analytical requirement of testing in regular time intervals (e.g., every hour or every few hours) whether sterile conditions are still maintained inside an isolator. By avoiding such costly requirements, production costs can be considerably reduced.

The liquid feeding device according to the invention is applicable for feeding droplets into different kinds of process lines for production of many formulations and/or compositions suitable for freeze-drying. This may include, for example, generally any hydrolysis-sensitive material. Suitable liquid formulations include, but are not limited to, antigens, adjuvants, vaccines, antibodies (e.g., monoclonal), antibody portions and fragments, other protein-based Active Pharmaceutical Ingredients (APIs) (e.g., DNA-based APIs, and cell/tissue substances), APIs for oral solid dosage forms (e.g., APIs with low solubility/bioavailability), fast dispersible or fast dissolving oral solid dosage forms (e.g., ODTs, orally dispersible tablets), and stick filled presentations, etc.

Also, with the deflection section for separating the droplets from each other by means of at least one gas jet of the liquid feeding device, some disadvantages which may occur further to the droplet separation by electrostatic charge of the droplets or the like may be avoided, such as the undesired sticking of the charged droplets to surfaces of a freeze-dryer.

BRIEF DESCRIPTION OF THE SEVERAL VIEWS OF THE DRAWINGS

Further aspects and advantages of the invention will become apparent from the following description of particular embodiments illustrated in the figures in which.

DESCRIPTION OF SPECIFIC EMBODIMENTS OF THE INVENTION

Figure 1:
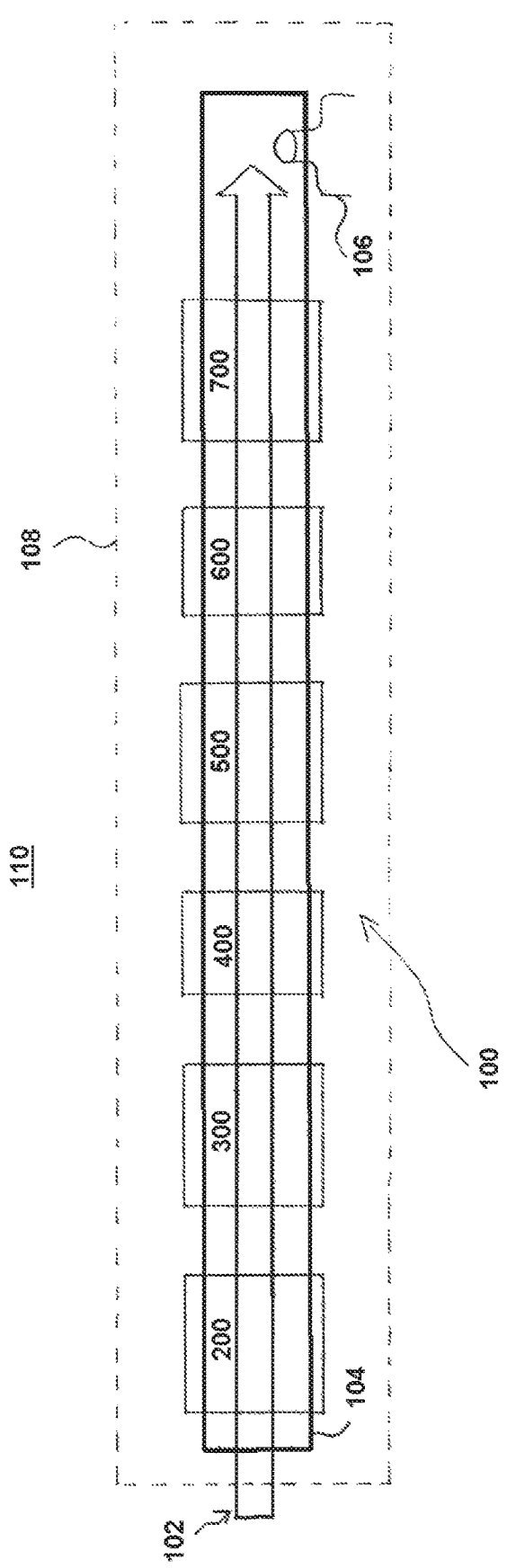
FIG. 1 is a schematic illustration of a product flow in a process line comprising a liquid feeding device according to a preferred embodiment of the invention.
Figure 2:
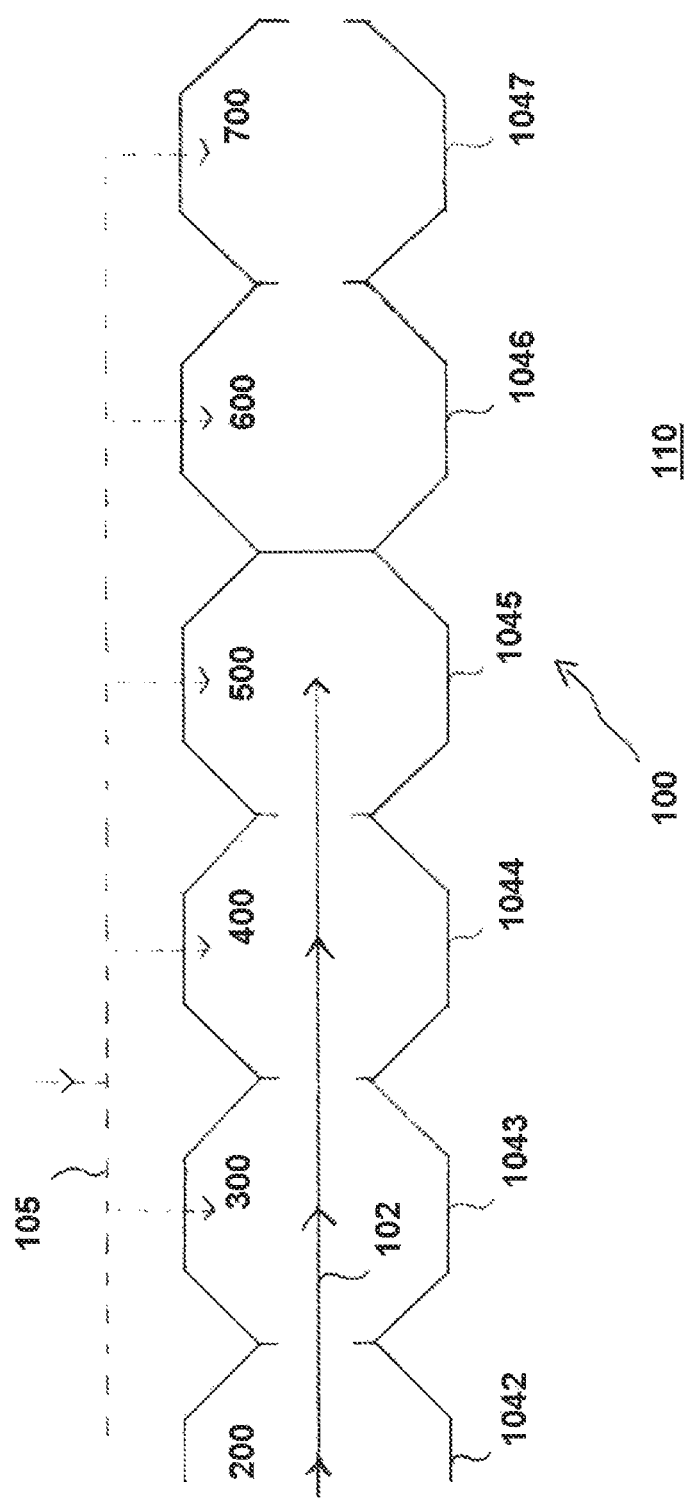
FIG. 2 is a schematic illustration of a configurational mode of the process line as illustrated on FIG. 1.

As a general overview, FIG. 1 schematically illustrates a process line 100 for the production of freeze-dried particles in the form of pellets, wherein a product flow 102 is assumed to pass through the process line 100 under closed conditions 104, also referred to as enclosure 104. A liquid feeding device 200 in accordance with a preferred embodiment of the present invention feeds liquid to a freezing chamber 300, also known as prilling chamber or prilling tower, in the form of ejected droplets (see also droplets 103 in FIG. 3), where the liquid is subjected to freeze-congealing. Frilling is a method of producing reasonably uniform spherical particles from liquid solutions. It essentially consists of two operations, firstly producing liquid droplets and secondly solidifying them individually by cooling. The prilling technology is also known as "laminar jet break-up" technology. The resulting frozen droplets are then transferred via a first transfer section 400 to a freeze-dryer 500 in which the frozen droplets are lyophilized. After lyophilization, the thus produced pellets are transferred via a second transfer section 600 to a discharge station 700, which provides for a filling of the pellets under closed conditions into final recipients 106, typically in the form of IBCs ("Intermediate Bulk Containers") which are then removed from the process line 100.

Enclosure 104 is intended to indicate that the product flow 102 from entry to exit of process line 100 is performed under closed conditions, i.e., the product is kept under sterility and/or containment. The process line provides closed conditions without the use of an isolator, the role of which is indicated by dashed line 108 which separates line 102 from environment 110. Instead of the need of an isolator, enclosure 104 separates product flow 102 from the surrounding environment 110, wherein enclosure 104 is implemented individually for each of the devices 200, 300, 500, 700 and transfer sections 400, 600 of process line 100. Thus, the object of end-to-end protection of sterility and/or containment of the product flow 102 in the entire process line 100 is achieved without putting the entire process within one single device, such as an isolator as known from prior art. Instead, the process line 100 according to the invention comprises separate process devices, e.g., one or more prilling tower, freeze-dryer, discharge station, etc., which are connected as indicated in FIG. 1 by one or more transfer sections 400, 600 to form an integrated process line 100 enabling an interface-free end-to-end (or start-to-end) product flow 102.

In an alternative view, FIG. 2 schematically illustrates the configuration of the process line 100 for the production of freeze-dried particles under closed conditions as shown in FIG. 1. Briefly, the product is flowing as indicated by arrow 102 and is preferably kept sterile and/or contained by accordingly operating each of the separate devices including liquid feeding device 200, freezing chamber 300, freeze-dryer 500 and first transfer section 400 under sterile conditions/containment, which is intended to be indicated by the respective enclosure parts 1042, 1043, 1045, and 1044 of enclosure 104. The discharge station 700, while not currently under operation in the shown state of process line 100, is also adapted for protecting sterility/providing containment by enclosure part 1047, and the second transfer section 600, while currently separating the devices 200, 300, 500 from the discharge station 700 in the shown state of process line 100, is also adapted for protecting sterility/providing containment by enclosure part 1046. Thus, in the exemplary configuration of the process line 100 as illustrated in FIG. 2, the first transfer section 400 is configured in an open state not to limit or interfere with the product flow 102, while the second transfer section 600 is configured to sealably separate the freeze-dryer 500 and discharge station 700, i.e., the second transfer section 600 operates to seal the freeze-dryer 500 and provide closed conditions 1046, 1047 in this respect.

Each of the devices 200, 300, 500, 700 and the transfer sections 400, 600 are separately adapted and optimized for operation under closed conditions, wherein "operation" refers to at least one mode of operation including, but not limited to, production of freeze-dried particles, or maintenance modes. Here, a sterilization of a process device or transfer section naturally also requires that the device/section is adapted to maintain sterility/containment. For example, as symbolized by CiP/SiP system 105 in FIG. 2, cleaning and/or sterilization of a process device or transfer section may not require any mechanical or manual intervention in that it is performed automatically in place throughout the process line 100 or in parts thereof. Automatic control of respective valves or similar separating means provided in association with the transfer sections, preferably by remote access thereto, also contribute to configurability of the process line 100 for different operational configurations without mechanical and/or manual intervention.

The details of how process devices such as freezing chambers or freeze-dryers can protect sterility and/or provide containment for the products processed therein depend on the specific application. For example, the sterility of a product is protected or maintained by sterilizing the involved process devices and transfer sections. It is to be noted that—after a sterilization process—a process volume confined within a hermetically closed wall will be considered sterile during a given time under particular processing conditions, such as, but not limited to, processing of the product under slight excess (positive) pressure compared to an environment 110. Containment can be considered to be achieved by processing the product under slightly lowered pressure compared to the environment 110. These and other appropriate processing conditions are known to the skilled person. As a general remark, transfer sections such as transfer sections 400, 600 depicted in FIGS. 1 and 2 have to ensure that product flow 102 through them is accomplished under closed conditions; this includes the aspect that closed conditions have to be ensured/maintained also for a transition of product into and out of the respective transfer section. In other words, an attachment or mounting of a transfer section to a device for achieving a product transfer has to preserve the desired closed conditions.

FIG. 3 illustrates a process line 100 as basically known from, for example, EP 2 578 974 A1, following the principles as described in regard to FIGS. 1 and 2. The process line 100 as shown in FIG. 3 is designed for the production of freeze-dried pellets under closed conditions, and is adapted to apply the liquid feeding device 200 according to the preferred embodiment of the present invention. The process line 100 substantially comprises a prilling tower as a specific embodiment of a freezing chamber 300, a freeze-dryer 500, and a discharge station 700. Here, the freezing chamber 300 and the freeze-dryer 500 are permanently connected to each other via a first transfer section 400, while the freeze-dryer 500 and the discharge station 700 are permanently connected to each other via a second transfer section 600. Each transfer section 400, 600 provides for product transfers between the connected process devices.

Figure 3:
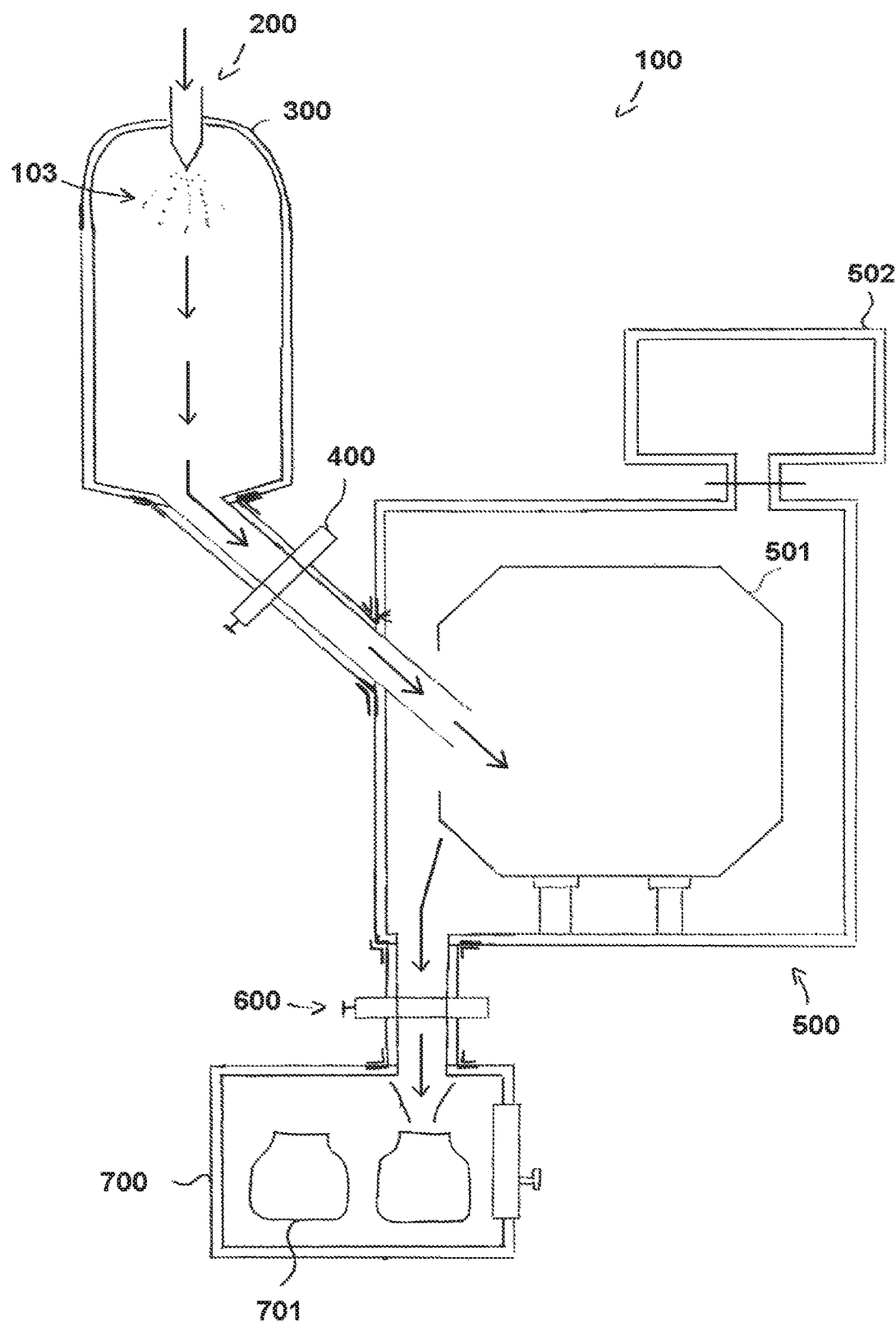
FIG. 3 shows an overall structure of a process line as illustrated in FIGS. 1 and 2.

The liquid feeding device 200 indicated only schematically in FIG. 3 is for providing the liquid product along the product flow 102 to the freezing chamber 300. Droplet generation by the liquid feeding device 200 into the freezing chamber 300 is affected by flow rate, viscosity at a given temperature, and further physical properties of the liquid to be ejected, as well as by the processing conditions of the atomizing process, such as the physical conditions of the spraying equipment including frequency, pressure, etc. Therefore the liquid feeding device 200 is adapted to controllably deliver the liquid and to generally deliver the liquid in a regular and stable flow. To this end, the liquid feeding device 200 can be connected to one or more liquid pumps. Any pump may be employed which enables precise dosing or metering. Examples for appropriate pumps may include, but are not limited to, peristaltic pumps, membrane pumps, piston-type pumps, eccentric pumps, cavity pumps, progressive cavity pumps, Mohno pumps, etc. Such pumps may be provided separately and/or as part of control devices such as pressure damping devices, which can be provided for an even flow and pressure at the entry point into the liquid feeding device 200. Alternatively or additionally, the liquid feeding device 200 may be connected to a temperature control device, for example a heat exchanger, for cooling the liquid in order to reduce the freezing capacities required within the freezing chamber 300. The temperature control device may be employed to control the viscosity of the liquid and in turn, in combination with the feed rate, influence the droplet size and/or droplet formation rate. The liquid feeding device 200 can have one or more flow meters connected upstream thereof for sensing the liquid feed rate. One or more filtration components can also be provided upstream of the liquid feeding device 200. Examples for such filtration components include, but are not limited to, mesh-filters, fabric filters, membrane filters, and adsorption filters. The liquid feeding device 200 can also be connected to a means configured to provide for sterility of the liquid to be ejected; additionally or alternatively, the liquid can be provided to the liquid feeding device 200 in presterilized form.

The freezing of the droplets 103 ejected and—thus—fed from the liquid feeding device 200 to the freezing chamber 300 may be achieved, for example, such that the diluted composition, i.e., the formulated liquid product, is prilled. "Prilling" may be defined as a frequency-induced break-up of a constant liquid droplet ejection jet into discrete droplets 103. Generally, the goal of prilling is to generate calibrated droplets 103 with diameter ranges for example from about 200 μm to about 1500 μm, with a narrow size distribution. For instance, the droplets may have a span equal or below about 1, preferably equal or below about 0.8, preferably equal or below about 0.7, preferably equal or below about 0.6, preferably equal or below about 0.4. The droplets 103 fall into the freezing chamber 300 in which a spatial temperature profile might be maintained with, for example a value of between −40° C. to −60° C., preferably between −50° C. and −60° C., in a top area and between −150° C. to −192° C., for example between −150° C. and −160° C., in a bottom area of the chamber 300. Lower temperatures may be reachable by cooling systems employing helium, for example. The droplets freeze during their fall in order to form preferably spherical, calibrated frozen particles, i.e. micropellets.

Cooling the inner volume of the freezing chamber 300 sufficiently for freezing the falling droplets 103 can be achieved by means of cooling the inner wall surface of the chamber 300 via a cooling medium conducting tubing or the like, and providing the freezing chamber 300 with an appropriate height. Therefore, a counter- or concurrent flow of cooled gas in the chamber's internal volume or other measure for direct cooling of falling droplets 103 can preferably be avoided. By avoiding contact of a circulating primary cooling medium such as a counter- or concurrent flow of gas with the falling product 103, the requirement of providing a costly sterile cooling medium is avoided when sterile production runs are desired. The cooling medium circulating outside the chamber's inner volume, for example in tubing or the like, need not to be sterile. A cooling medium may be, for example, liquid nitrogen. In one embodiment, the freezing chamber 300 may comprise—with regard to the direction of the droplet flow—a counter-current flow or a concurrent flow of a cooling medium. In another embodiment, the freezing chamber 300 may be devoid of any counter-current or concurrent flow of cooling medium. In such a case, the congealing or freezing of the droplets is ensured by the cooling of the inner wall of the chamber. The droplets 103 are frozen on their gravity-induced fall within the freezing chamber 300 due to cooling mediated by the temperature-controlled wall chamber 300 and an appropriate non-circulating atmosphere provided within the internal volume, for example, an (optionally sterile) nitrogen and/or air atmosphere. As an example, in the absence of further cooling mechanisms, for freezing droplets 103 into substantially spherical micropellets with diameters in the range of 200-800 μm, an appropriate height of the prilling tower might be 1-2 m, while for freezing droplets into pellets with a size range up to 1500 μm, the prilling tower can have a height of about 2-3 m, wherein the diameter of the prilling tower can be between about 50-150 cm for a height of 200-300 cm. The temperatures in the prilling tower can optionally be maintained or varied/cycled throughout between about −50° C. to −190° C.

The frozen droplets 103 reaching the bottom of the chamber 300 are then automatically transferred by gravity towards and into the first transfer section 400, from where the frozen droplets 103 are transferred into a rotary drum 501 of the freeze-dryer 500, in which sublimation of the frozen droplets 103 results in freeze-dried pellets under vacuum conditions generated by a vacuum pump for providing a vacuum in the internal volume of the freeze-dryer 500 and, thus, the internal volume of the drum 501. Afterwards, the freeze-dried pellets are transferred via the second transfer section 600 into the discharging station 700, in which the freeze-dried pellets are filled into vials 701 for shipping.

Figure 4:
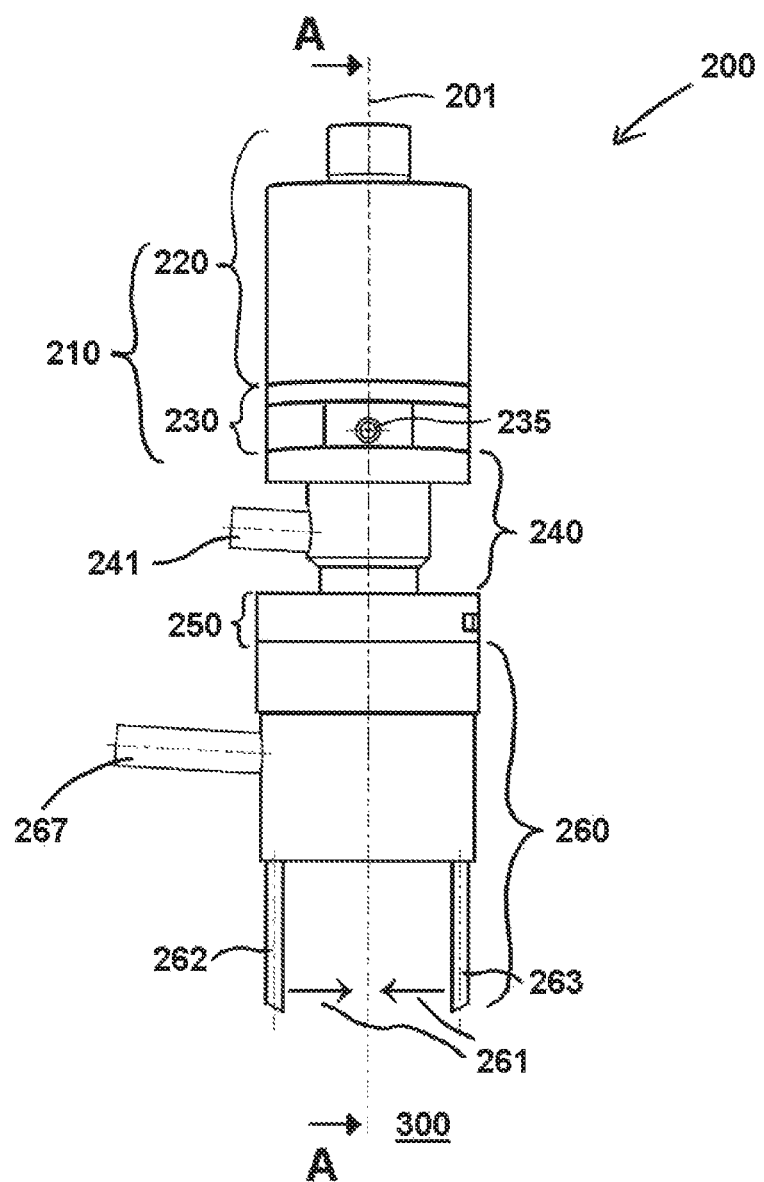
FIG. 4 shows a side view of the liquid feeding device according to the preferred embodiment of the invention.

FIG. 4 shows the liquid feeding device 200 according to the preferred embodiment of the invention, which liquid feeding device 200 comprises a droplet ejection section 210 with an actuation portion 220 and a nozzle portion 230, a CiP/SiP section 240, a droplet counting section 250 and a deflection section 260, in this order from top to bottom of the drawing. The order of the sections of the liquid feeding device 200 from top to bottom, i.e. from section 210 to section 260 coincides with the direction of product flow inside the liquid feeding device 200. In general, the actuation portion 220 of the droplet ejection section 210 serves for generating magnetic waves by alternating positive and negative magnetizations of a coil, which waves are used for effecting magnetic impulses resulting in an ejection of droplets from the nozzle portion 230 of the droplet ejection section 210. Here, an outlet port 235 of the nozzle portion 230 can also be gathered from FIG. 4, which outlet port 235 will be described later in further detail.

The subsequently arranged CiP/SiP section 240 serves for cleaning and/or sterilizing the interior of the liquid feeding device 200, preferably by introducing steam into the liquid feeding device 200, thereby achieving steam pressure sterilization of the parts of the interior of the liquid feeding device 200 penetrable by the steam. Here, the steam can be introduced by inlet 241 into the CiP/SiP section 200 from the outside, wherein the inlet 241 can be connected to any kind of fluid delivering means, such as a steam pressure pump or the like for SiP procedures, or to a cleaning fluid pump or the like for CiP procedures. The droplet counting section 250 following the CiP/SiP section 240 serves for counting the generated droplets, wherein the CiP/SiP section 240 requires a predetermined length in order to provide sufficient travelling distance, such as 30 mm to 50 mm, for the ejected liquid jet to separate in an ejection direction into separate droplets.

The droplet counting section 250 utilizes an optical device for optically registering the droplets passing through, such as a glass cylinder comprising light emitting optical fibers and light receiving optical fibers arranged opposite to each other across the area through which the droplets pass. Finally, the liquid feeding device 200 of the preferred embodiment comprises a deflection section 260 arranged subsequently to the droplet counting section 250, the deflection section 260 employing at least one gas jet 261 directed towards the droplet ejection path 211, wherein the gas jet 261 is discharged by deflection tubes 262, 263. The droplet counting section 250 can also be positioned at another location along the travel path of the droplets, as long as the necessary travelling distance of 30 to 50 mm required for the liquid jet to separate into droplets is maintained. The fluid for generating the gas jet 261 is introduced into the deflection section 260 and, thus, into the deflection tubes 262, 263 through a deflection gas inlet 267 which can be connected to any kind of gas delivering means, such as a gas pump or the like. The introduced gas can be air or alternatively any inert gas, such as any one of Nitrogen, Helium, Argon or Xenon, or the like. Here, a droplet ejection path 211 (see FIG. 7a) basically coincides with the longitudinal axis 201 of the liquid feeding device 200. In general, the CiP/SiP section 240, the droplet counting section 250 and the deflection section 260 each comprises a respective recess passing therethrough, wherein these recesses are connected with each other such that the droplets ejected from the droplet ejection section 210 can pass through the sections 240, 250 and 260 in order to exit the liquid feeding device 200 at its lower end, passing by the deflection tubes 262, 263 such that the droplets interact with the gas jet 261.

The mounting of the entire liquid feeding device 200 needs to ensure that all of its sections 210, 240, 250 and 260 are in vertical alignment, in particular in order to achieve the intersection of the ejected droplets, i.e. the droplet ejection path with the at least one deflection gas jet 261. In practice, the different sections can be attached to each other by known means such as clamping components, screws or the like, and the transition areas between the different sections can be provided with known sealing elements, such as O-Rings or the like, in order to maintain closed conditions. The alignment of the different sections to each other can be achieved for example by known centering means, such as a combination of centering bores and respective centering protrusions at the transition areas of the single sections. In order to reduce the technical detail of the drawings, these known components (O-rings, screws, centering protrusions, etc.) have been omitted in the drawings for the sake of a clearer overview.

Figure 5:
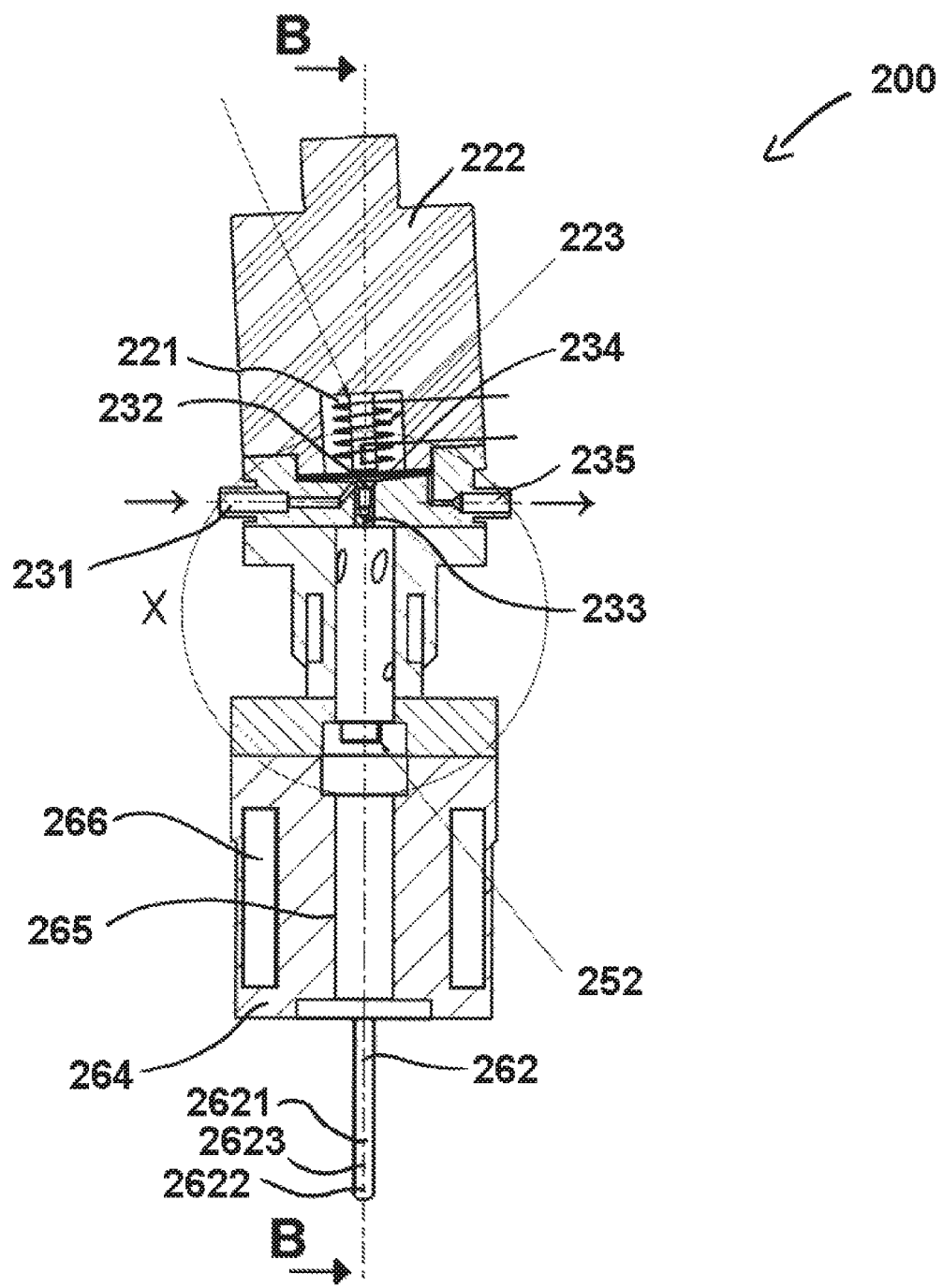
FIG. 5 is a cross-sectional view of the liquid feeding device of FIG. 4 along line A-A.

FIG. 5 shows a cross-section of the liquid feeding device 200 along the line A-A in FIG. 4. Here, it can be gathered that the actuation portion 220 consists of an excitation unit 221 and a main body 222 consisting of antimagnetic material, such as plastic material (PTFE, i.e. Teflon, or the like), Aluminum, non-magnetic stainless steel or the like, wherein the excitation unit 221 basically consists of an electromagnetic coil 223 and a coil core arranged there inside, such as an iron core or the like. The combination of electromagnetic coil 223 and coil core act as a simple electromagnet for applying a magnetic force to a magnetic force receiving member, here in the form of a membrane 234 of the nozzle portion 230. The detailed structure of the nozzle portion 230 of the droplet ejection section 210 can be gathered from FIG. 7a, in which the detail "X" as indicated in FIG. 5 is shown in an enlarged view. From FIG. 7a, it can be gathered that the nozzle portion 230 comprises an inlet port 231, a liquid chamber 232 having a cross axis or lateral axis 2321 and a longitudinal axis 2322 and being arranged in an inclined manner, a nozzle 233 through which the liquid from the liquid chamber 232 is ejected, the mentioned membrane 234 constituting one side of the liquid chamber 232, the outlet port 235, also referred to as bypass or bypass port, and a main body 236 of the nozzle portion 230, in which the inlet port 231, the liquid chamber 232, the nozzle 233, the membrane 234 and the outlet port 235 are accommodated. Furthermore, the nozzle 233 is provided in a nozzle body 237 for manufacturing reasons, such that a nozzle orifice 2331 opens into a central through-hole provided in the CiP/SiP section 240, and the nozzle orifice 2331 is connected to the liquid chamber by a nozzle channel 2332. The nozzle 233 comprises a longitudinal axis 2333 proceeding coaxially to the droplet ejection path 211 and to the longitudinal axis 201 of the liquid feeding device 200. Here, the liquid chamber 232 is arranged in an inclined manner such that its longitudinal axis 2322 is tilted in regard to the longitudinal axis 2333 of the nozzle 233, preferably with an extend of 2-5°, further preferably 3°. The nozzle body 237 is permanently installed/inbuilt in a central through-hole 2361 provided in the main body 236, wherein the nozzle body can be attached to the main body 236 by laser-welding or the like.

Figure 8:
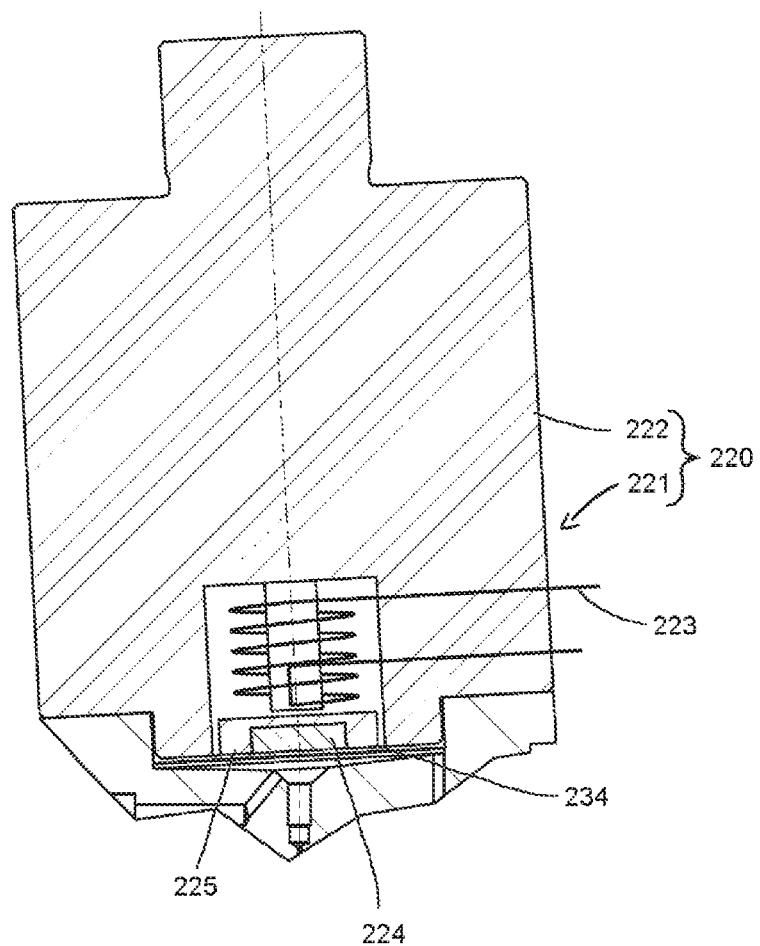
FIG. 8 is an enlarged view of the respective parts of an alternative structure of the actuation portion of the liquid feeding device according to the preferred embodiment of the invention.

In FIG. 8, a further development of the actuation portion 220 can be gathered, which is applicable to the liquid infeed device 200 of the preferred embodiment. In the further developed actuation portion 220, the excitation unit 221 comprises a combination of a cylindrically shaped permanent magnet 224 separably attachable to the membrane 234 opposite the liquid chamber 232 and the above mentioned combination of electromagnetic coil 223 and coil core acting as a simple electromagnet. A damping element 225 in the form of an inverted U-shape, i.e. in the form of an inverted cup-shape, is provided around the permanent magnet 224 with its cup-bottom between the magnet 224 and the coil-coil core combination for achieving a damping effect between the magnet 224 and the coil 223, wherein the damping element 225 can be made out of silicone. The damping element 225 is provided basically in a cup-shaped manner in a way that the electromagnetic coil 223 and the magnet 224 all have defined positions in relation to each other. The damping element 225, also referred to as damper, can increase the displacement of the magnet 224, the damping element 225 covering the transversal circumference of the magnet 224, thereby arranging the magnet 224 inside the inner recess of the damping element 225 in a way that the magnet 224 can be just mounted centrically in regard to the damping element 225 and, thus, in regard to the electromagnetic coil 223, to avoid any tilting of the magnet 224 or its contact with the coil 223 or the coil core, resulting in the desired damping effect.

The inlet port 231 opens into the liquid chamber 232 near the intersection between liquid chamber 232 and nozzle channel 2332. The outlet port 235 opens into the liquid chamber 232 at an outer circumference of the liquid chamber 232 at the highest possible position due to the tilting of the liquid chamber 232, such that liquid in the liquid chamber 232 may only exit the liquid chamber 232 through the outlet port 235 in case the liquid chamber 232 is entirely filled with liquid and the outlet port 235 enables a drainage of the liquid. The inlet port 231 can be connected to a liquid source, such as a pressurized liquid tank, a peristaltic pump or the like, wherein a pressurized liquid tank is a preferred option since no pressure fluctuations of the infed liquid occur due to the constant pressure inside the tank, wherein a peristaltic pump can exhibit pressure fluctuations of the infed liquid. The outlet port 235, on the other hand, can be connected to a drain tank, drain tubing, a liquid collection container or the like, wherein a blocking means can be provided subsequently to the outlet port 231, such as a check valve, a shut-off valve or the like. During droplet generation, i.e. droplet ejection into the freezing chamber 300, the liquid transferred through the liquid inlet port 231 into the liquid chamber 232 is the liquid to be ejected, such as, for example, antigens, adjuvants, vaccines, antibodies, APIs, ODTs, blood plasma components, or the like. However, since it is not or only insufficiently possible to provide CiP/SiP fluid from the CiP/SiP section 240 into the liquid chamber 232 through the nozzle orifice 2331 due to its minute inner diameter, the inlet port 231 can also be used to provide such CiP/SiP fluid through the inlet port 231 into the liquid chamber 232 and out of the outlet port 235, wherein the large diameters of the ports 231, 235 (large compared to the diameter of the nozzle orifice 2331) allow a substantial CiP/SiP fluid flow volume, resulting in excellent CiP/SiP results of the droplet ejection section 210 without the need of disassembling the liquid feeding device 200. Here, as an example of dimensions, the diameter of the liquid inlet port 231 can reside in a range of 0.9 mm to 1.3 mm, preferably 1.1 mm, and the diameter of the outlet port 235 can reside in a range of 0.8 mm to 1.2 mm, preferably 1.0 mm. Compared to an exemplary diameter of the nozzle orifice 2331 of about 300 µm, this results in a diameter ratio port/orifice of about 3:1 to 4:1.

Figure 7B:
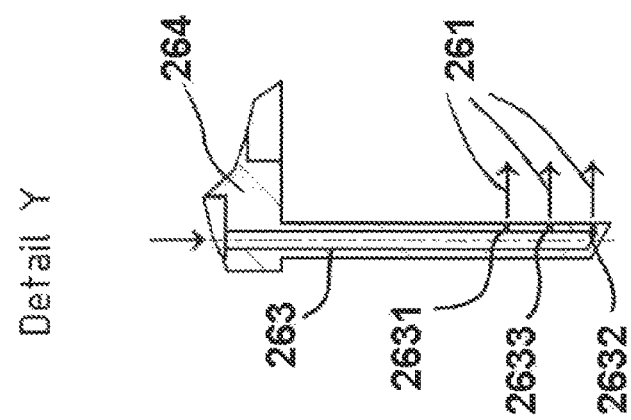
FIG. 7b is an enlarged view of detail "Y" in FIG. 6, illustrating one deflection tube of the liquid feeding device according to the preferred embodiment of the invention in cross-section.
Figure 7A:
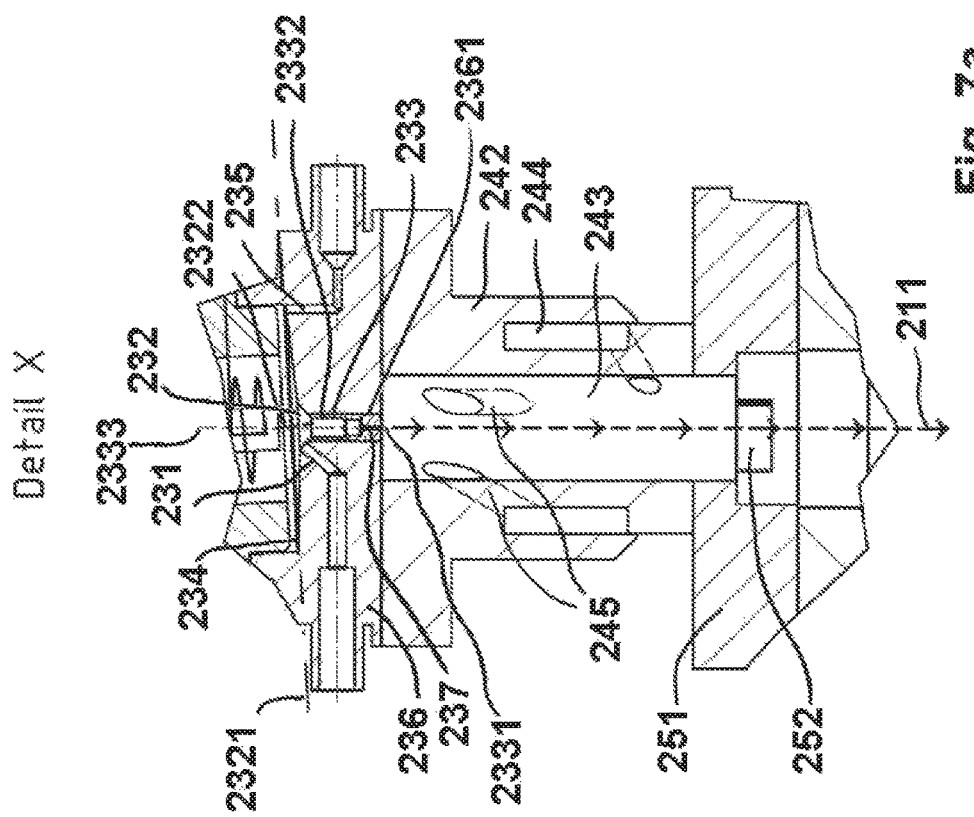
FIG. 7a is an enlarged view of detail "X" in FIG. 5.

As can also be gathered from FIG. 7a in detail, besides the inlet 241, the CiP/SiP section 240 consists of a main body 242 sandwiched between the nozzle portion main body 236 as well as a main body 264 of the deflection section 260. In the CiP/SiP section main body 242, a central through-hole 243 as a transition zone for the droplets is provided as a straight bore hole in a cylindrical form. Furthermore, a fluid chamber 244 is provided in the main body 242, which fluid chamber 244 is arranged circumferentially around the through-hole 243, wherein the fluid chamber 244 is connected to the inside of the through-hole 243 by several fluid channels 245 for providing the CiP/SiP fluid coming from the inlet 241 into the through-hole 243 of the CiP/SiP section 240 and, thus, into the sections connected to the CiP/SiP section 240, such as the droplet counting section 250 and the deflection section 260. The fluid channels 245 are preferably provided in an inclined manner such that they open into the through-hole 243 with an angle, thereby providing any CiP/SiP fluid streamed into the through-hole 243 with a spin, resulting in an improved cleanability/sterilizability effect of the CiP/SiP section 240 and, thus, the other sections of the liquid feeding device 200 fluid-connected to the CiP/SiP section 240. Also, in addition, the inclined fluid channels 245 can be used to inject gas with the purpose of interfering with the ejected droplets on their ejection path 211 such that the separation of the droplets can be further promoted.

In the direction of the droplet path 211, subsequently to the CiP/SiP section 240, the droplet counting section 250 is arranged, wherein the droplet counting section 250 comprises a main body 251 and an optical counting component 252. Here, the optical counting component 252 can be sandwiched between two parts of the main body 251 for the sake of simplified installation. The optical counting component 252 of the preferred embodiment can be a see-through glass tube with ports for fibre optics (not shown in detail), wherein the fibre optics serve for counting the droplets by means of an optical sender and an optical receiver, in between of which the ejected droplets pass through. In particular, the glass tube can be introduced as a glass cylinder integrated into a flange that carries opening ports to take up a light emitting sender and a respective receiver for registering the droplets passing through, the flange being sandwiched between the mentioned parts of the main body 251.

Figure 6:
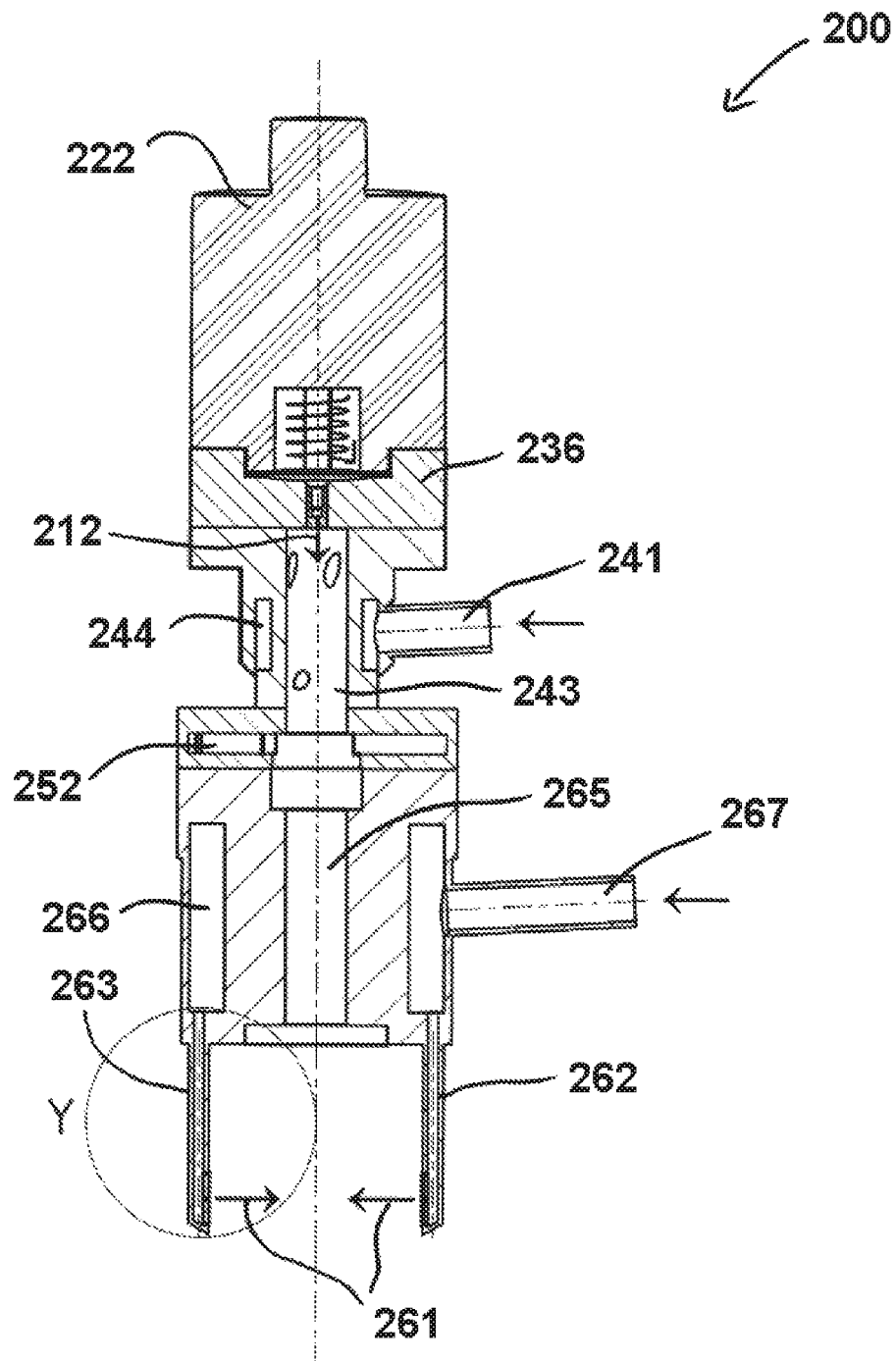
FIG. 6 is a cross-sectional view of the liquid feeding device of FIGS. 4 and 5 along line B-B in FIG. 5.

As a further part of the liquid feeding device 200 which can be gathered from FIGS. 5 and 6, the deflection section 260 follows the droplet counting section 250 in an ejection direction 212 of the liquid and, thus, of the ejected droplets, wherein the deflection section 260 serves for spreading the droplets, i.e. separating the droplets from each other by means of the at least one gas jet 261 in order to avoid coalescence of the droplets prior to freezing and to improve the heat transfer. The at least one gas jet 261 of the deflection section 260 is provided by two deflection tubes, deflection tube 262 and deflection tube 263, which are arranged directly opposite to each other, with the droplet ejection path 211 proceeding in between. As already mentioned above, the fluid for generating the gas jet 261 is introduced into the deflection section 260 through a main body 264 and, thus, into the deflection tubes 262, 263 through the deflection gas inlet 266 which can be connected to any kind of gas delivering means, such as a gas pump or the like. The gas jet 261 is directed towards the droplet ejection path 211 such that the gas jet 261 or better the several gas jets 261 of the preferred embodiment impact on the ejected droplets on the ejection path 2111 with a right angle.

Therefore, as can be gathered from FIG. 7b in detail, each deflection tube 262, 263 is hollow and comprises several gas jet outlet ports, i.e. the deflection tube 262 comprises three gas jet outlet ports 2621, 2622, 2623, and the deflection tube 263 comprises three gas jet outlet ports 2631, 2632, 2633. The outlet ports 2621, 2622, 2623 connect the hollow interior of tube 262 with the outside, and the outlet ports 2631, 2632, 2633 connect the hollow interior of tube 263 with the outside, i.e. with the interior of the freezing chamber 300. Here, the uppermost gas jet outlet port 2631 of deflection tube 263 is arranged directly opposite to the uppermost gas jet outlet port 2621 of deflection tube 262, the middle gas jet outlet port 2633 of deflection tube 263 is arranged directly opposite to the middle gas jet outlet port 2623 of deflection tube 262, and the lowest gas jet outlet port 2632 of deflection tube 263 is arranged directly opposite to the lowest gas jet outlet port 2622 of deflection tube 262, in an order from top to bottom in the ejection direction 212. The lowest gas jet outlet port 2622, 2632 of each deflection tube 262, 263 is arranged at its tip and connects with a respective interior of each tube 262, 263 at its edge, such that each deflection tube 262, 263 is self-draining, meaning that any fluid in each tube 262, 263 is drained therefrom through the respective lowest gas jet outlet port 2622, 2632 by means of gravity. In order to provide the gas jet fluid to the deflection tubes 262, 263, the hollow interior of each tube 262, 263 is fluid-connected with a fluid chamber 266 provided in the main body 264, which fluid chamber 266 is connected to the gas inlet 266 and is arranged circumferentially around a central through-hole 265 provided in the main body 264 for letting the droplets pass through the deflection section's main body 264.

According to the preferred embodiment of the liquid feeding device 200 of the present invention, the main body 264 is an integral component. However, in accordance with a further embodiment, the main body 264 can also consist of several parts being mechanically connected, for example in the form of a clamping means, screws or the like, wherein the inside of the main body 264, i.e. the inside of the fluid chamber 266 needs to be fluid-tightly closed against the outside, for example by means of a sealing component such as an O-ring, a gasket or the like. Moreover, according to the preferred embodiment of the liquid feeding device 200 of the present invention, the central through-hole 265 as a transition zone for the droplets is provided in the form of a straight bore hole centrally extending throughout the main body 264 in a cylindrical form. However, in accordance with a further embodiment, the central through-hole 265 can also exhibit a conical shape, with an increasing diameter in the ejection 212 towards the deflection tubes 262, 263. Here, the opening of the diameter of the conical shape is preferably chosen to avoid any deposition of small droplets, so called satellites, in the area of the central through-hole.

Figure 9:
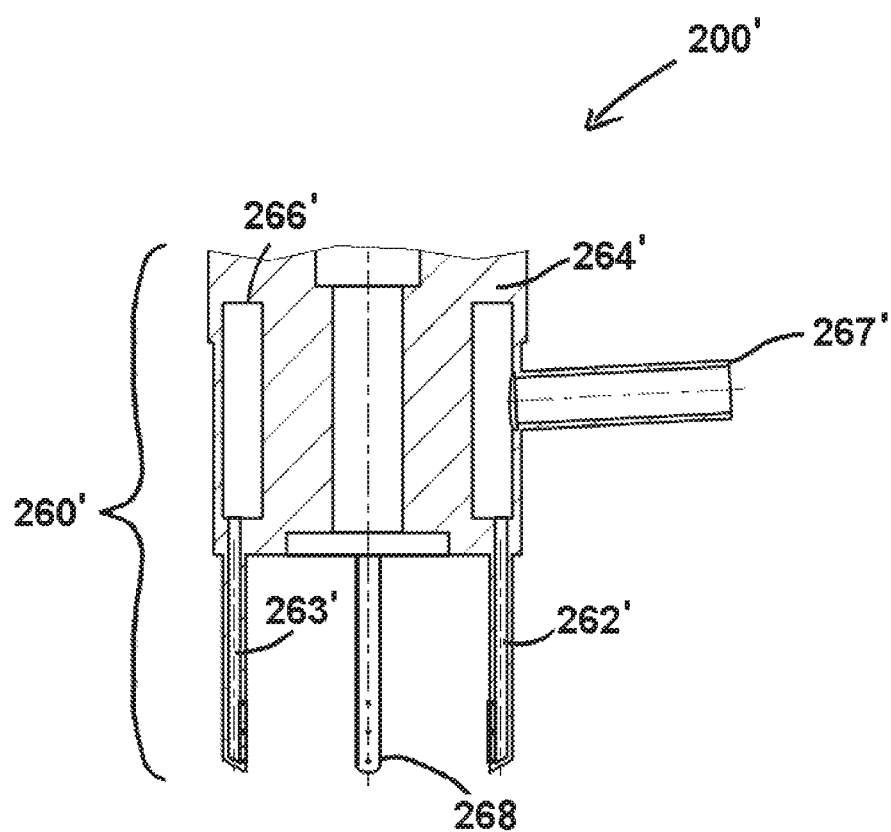
FIG. 9 is an enlarged view of a deflection section of a liquid feeding device according to another preferred embodiment of the invention in cross-section.

FIG. 9 shows a modification of the deflection section of the liquid feeding device according to the above described preferred embodiment of the invention, i.e. another preferred embodiment of the invention. In order to avoid redundancy, some of the components provided identical to the above described preferred embodiment are not shown or further described but are to be understood as having the same technical structure and functionality. Contrary to the above described embodiment of the liquid feeding device 200, the deflection section 260' of the shown embodiment of the modified liquid feeding device 200' comprises four deflection tubes, i.e. deflection tube 262', deflection tube 263', deflection tube 268 and a further deflection tube (not shown) instead of the two deflection tubes 262, 263 of the above described embodiment. Due to the cross-sectional view in FIG. 9, only three of the four deflection tubes of the present embodiment are shown in FIG. 9, i.e. deflection tubes 262', 263' and 268, whereas the fourth deflection tube is not shown. Similar to the above described deflection section 260, the deflection section 260' is arranged subsequently to a droplet counting section of the liquid feeding device 200', and the deflection section 260' employs at least four gas jets generated from the four deflection tubes, which jets are directed towards a droplet ejection path. The fluid for generating the gas jets is introduced into the deflection section 260' and, thus, into the deflection tubes through a deflection gas inlet 267' which can be connected to any kind of gas delivering means, such as a gas pump or the like, which provides the introduced gas such as air or alternatively any inert gas, such as any one of Nitrogen, Helium, Argon or Xenon, or the like. Similarly to the deflection section 260, the deflection section 260' serves for spreading the droplets, i.e. separating the droplets from each other by means of the at least one gas jet in order to avoid coalescence of the droplets prior to freezing and to improve the heat transfer. The four gas jets of the deflection section 260' are provided by the four deflection tubes, wherein deflection tube 262' and deflection tube 263' are arranged directly opposite to each other, and wherein deflection tube 268 and the further deflection tube (not shown) are arranged directly opposite to each other, with the droplet ejection path proceeding in between at the cross section of the gas jets produced by the four deflection tubes. The fluid for generating the gas jets is introduced into the deflection section 260' through a main body 264' and, thus, into the deflection tubes through the deflection gas inlet 266' which is connected to the deflection gas inlet 267'.

The gas jets are directed towards the droplet ejection path such that the gas jets impact on the ejected droplets on the ejection path with a right angle to the longitudinal axis of the ejection section 260'. In order to be able to do so, each deflection is hollow and comprises one or several gas jet outlet ports which connect the hollow interior of each tube with the outside, i.e. with an interior of a freezing chamber of the process line. The gas jet outlet ports of each deflection tube can be provided similarly to the above described embodiment, i.e. with a number of one or several, e.g. three outlet ports for each deflection tube, the ports being arranged above each other on the same longitudinal axis. However, it is considered to be understood that the number of the outlet ports can be one, two, three, four etc., in each deflection tube, as desired, in order to provide as many gas jets as desired. Also, in the present embodiment, four deflection tubes are arranged in a way such that sets of two deflection tubes are arranged opposite to each other, resulting in a crosswise arrangement in the same plane, i.e. in an equiangular arrangement of 90° between two adjacent tubes. Thereby, the respective gas jets on each level of outlet ports meet each other at the droplet ejection path in a rectangular manner.

As a modification thereof, only three tubes can also be provided, wherein the tubes are then to be arranged again in an equiangular manner, i.e. with 120° between two adjacent tubes. Moreover, five or more tubes could also be provided in an equiangular manner as a further modification, if desired. As a further alternative embodiment, it is conceivable that all provided gas jet outlet ports are directed to one and the same location on the droplet ejection path, thereby gathering the deflection force of all provided gas jets on the same spot.

The products resulting from a process line 100 applying a liquid feeding device 200 or a liquid feeding device 200' according to the invention can comprise virtually any formulation in liquid or flowable paste state that is suitable also for conventional (e.g., shelf-type) freeze-drying processes, for example, monoclonal antibodies, protein-based APIs, DNA-based APIs; cell/tissue substances; vaccines; APIs for oral solid dosage forms such as APIs with low solubility/bioavailability; fast dispersible oral solid dosage forms like ODTs, orally dispersible tablets, stick-filled adaptations, etc., as well as various products in the fine chemicals and food products industries. In general, suitable flowable materials for prilling include compositions that are amenable to the benefits of the freeze-drying process (e.g., increased stability once freeze-dried).

The invention improves the generation of, for example, sterile lyophilized and uniformly calibrated particles, e.g., micropellets, as bulkware. The resulting product can be free-flowing, dust-free and homogeneous. Such products have good handling properties and can be easily combined with other components, wherein the components might be incompatible in liquid state or only stable for a short time period and thus otherwise not suitable for conventional freeze-drying.

In order to support a permanently mechanically integrated system providing end-to-end sterility and/or containment, additionally, a specific cleaning concept for the liquid feeding device of the present invention is contemplated. In a preferred embodiment, a single steam generator, or a similar generator/repository for a cleaning and/or sterilization medium can be provided The cleaning/sterilization system of the liquid feeding device of the present invention can be configured to perform automatic CiP/SiP for different sections of the device or of the entire device, which avoids the necessity of complex and time-consuming cleaning/sterilization processes requiring a disassembly of the liquid feeding device and/or which have to be performed at least in part manually.

The products resulting from the use of the liquid feeding device according to the invention can comprise virtually any formulation in liquid or flowable paste state that is suitable also for conventional (e.g., shelf-type) freeze-drying processes, for example, monoclonal antibodies, protein-based APIs, DNA-based APIs, cell/tissue substances, vaccines, APIs for oral solid dosage forms such as APIs with low solubility/bioavailability, fast dispersible oral solid dosage forms like ODTs, orally dispersible tablets, stick-filled adaptations, etc., blood plasma components, as well as various products in the fine chemicals and food products industries.

In general, suitable flowable materials for prilling include compositions that are amenable to the benefits of the freeze-drying process (e.g., increased stability once freeze-dried). The invention allows the generation of, for example, sterile lyophilized and uniformly calibrated particles, e.g., micropellets, as bulkware. The resulting product can be free-flowing, dust-free and homogeneous. Such products have good handling properties and can be easily combined with other components, wherein the components might be incompatible in liquid state or only stable for a short time period and thus otherwise not suitable for conventional freeze-drying. Freeze-drying in the form of particles, particularly in the form of micropellets allows stabilization of, for example, a dried vaccine product as known for mere freeze-drying alone, or it can improve stability for storage. The freeze-drying of bulkware (e.g., vaccine or fine chemical micropellets) offers several advantages in comparison to conventional freeze-drying; for example, but not limited to, the following: it allows the blending of the dried products before filling, it allows titers to be adjusted before filling, it allows minimizing the interaction(s) between any products, such that the only product interaction occurs after rehydration, and it allows in many cases an improvement in stability.

In fact, the product to be bulk freeze-dried can result from a liquid containing, for example, antigens together with an adjuvant, the separate drying of the antigens and the adjuvant (in separate production runs, which can, however, be performed on the same process line according to the invention), followed by blending of the two ingredients before the filling or by a sequential filling. In other words, the stability can be improved by generating separate micropellets of antigens and adjuvant, for example. The stabilizing formulation can be optimized independently for each antigen and the adjuvant. The micropellets of antigens and adjuvant can subsequently be filled into the final recipients or can be blended before filling into the recipients. The separated solid state allows one to avoid throughout storage (even at higher temperature) interactions between antigens and adjuvant. Thus, configurations might be reached, wherein the content of the vial can be more stable than any other configurations. Interactions between components can be standardized as they occur only after rehydration of the dry combination with one or more rehydrating agents such as a suitable diluent (e.g., water or buffered saline).

A subject-matter of the invention is relating to a process for preparing a vaccine composition comprising one or more antigens in the form of freeze-dried particles comprising at least a step of generating liquid droplets of said vaccine composition with a liquid feeding device 200, 200' according to the invention. The obtained droplets are further subjected to a step of freeze-drying to obtain freeze-dried particles. The freeze-dried particles may optionally be filled into a recipient.

A subject-matter of the invention is relating to a process for preparing a composition comprising one or more adjuvant(s) in the form of freeze-dried particles comprising at least a step of generating liquid droplets of said composition with a liquid feeding device 200, 200' according to the invention. The obtained droplets are further subjected to a step of freeze-drying to obtain freeze-dried particles. The freeze-dried particles may optionally be filled into a recipient.

In a further aspect, the invention is relating to a process for preparing an adjuvant containing vaccine composition comprising one or more antigens in the form of freeze-dried particles comprising at least a step of generating liquid droplets of said vaccine composition with a liquid feeding device according to the invention, or at least the steps of generating liquid droplets of an antigen(s)-containing composition with a liquid feeding device according to the invention, of generating liquid droplets of an adjuvant-containing composition with a liquid feeding device according to the invention, freeze-drying the droplets to obtain freeze-dried particles, and blending the freeze-dried particles of antigen(s) with the freeze-dried particles of adjuvant.

Another subject-matter of the invention is relating to a process for preparing a vaccine composition comprising one or more antigens in the form of freeze-dried particles comprising at least the steps of generating liquid droplets of a liquid bulk solution comprising an adjuvant and one or more antigens with a liquid feeding device according to the invention, freeze-drying the obtained droplets, and, optionally, filling the freeze-dried particles obtained into a recipient.

Alternatively when the one or more antigens and the adjuvant are not in the same solution, the process for preparing an adjuvant containing vaccine composition comprises at least the steps of generating liquid droplets of a liquid bulk solution comprising an adjuvant, generating liquid droplets of a liquid bulk solution comprising one or more antigens, wherein the liquid droplets generated at one of the steps before being generated with a with a liquid feeding device according to the invention, freeze-drying the obtained liquid droplets to obtain freeze dried particles of said one or more antigens and freeze dried particles of said adjuvant, blending the freeze dried particles of said one or more antigens with the freeze dried particles of said adjuvant, and, optionally, filling the blending of freeze-dried particles into a recipient.

The liquid bulk solution of antigen(s) may contain for instance killed, live attenuated viruses or antigenic component of viruses like Influenza virus, Rotavirus, Flavivirus (including for instance dengue (DEN) viruses serotypes 1, 2, 3 and 4, Japanese encephalitis (JE) virus, yellow fever (YF) virus and West Nile (WN) virus as well as chimeric Flavivirus), Hepatitis A and B virus, Rabies virus. The liquid bulk solutions of antigen(s) may also contain killed, live attenuated bacteria, or antigenic component of bacteria such as bacterial protein or polysaccharide antigens (conjugated or non-conjugated), for instance from serotype b *Haemophilus influenzae, Neisseria meningitidis, Clostridium tetani, Corynebacterium diphtheriae, Bordetella pertussis, Clostridium botulinum, Clostridium difficile*. A liquid bulk solution comprising one or more antigens means a composition obtained at the end of the antigen production process. The liquid bulk solution of antigen(s) can be a purified or a non purified antigen solution depending on whether the antigen production process comprises a purification step or not. When the liquid bulk solution comprises several antigens, they can originate from the same or from different species of microorganisms. Usually, the liquid bulk solution of antigen(s) comprises a buffer and/or a stabilizer that can be for instance a monosaccharide such as mannose, an oligosaccharide such as sucrose, lactose, trehalose, maltose, a sugar alcohol such as sorbitol, mannitol or inositol, or a mixture of two or more different of these aforementioned stabilizers such as a mixture of sucrose and trehalose. Advantageously, the concentration of monosaccharide oligosaccharide, sugar alcohol or mixture thereof in the liquid bulk solution of antigen(s) ranges from 2% (w/v) to the limit of solubility in the formulated liquid product, more particularly it ranges from 5% (w/v) to 40% (w/v), 5% (w/v) to 20% (w/v) or 20% (w/v) to 40% (w/v). Compositions of liquid bulk solutions of antigen(s) containing such stabilizers are described in particular in WO 2009/109550, the subject-matter of which is incorporated by reference. When the vaccine composition contains an adjuvant it can be for instance:

1) a particulate adjuvant such as: liposomes and in particular cationic liposomes (e.g. DC-Choi, see e.g. US 2006/0165717, DOTAP, DDAB and 1,2-Dialkanoyl-sn-glycero-3-ethylphosphocholin (EthyIPC) liposomes, see U.S. Pat. No. 7,344,720), lipid or detergent micelles or other lipid particles (e.g. Iscomatrix from CSL or from Isconova, virosomes and proteocochleates), polymer nanoparticles or microparticles (e.g. PLGA and PLA nano- or microparticles, PCPP particles, Alginate/chitosan particles) or soluble polymers (e.g. PCPP, chitosan), protein particles such as the *Neisseria meningitidis* proteosomes, mineral gels (standard aluminum adjuvants: AlOOH, AlPO4), microparticles or nanoparticles (e.g. Ca3(P04)2), polymer/aluminum nanohybrids (e.g. PMAA-PEG/AlOOH and PMAA-PEG/AlPO4 nanoparticles) O/W emulsions (e.g. MF59 from Novartis, AS03 from GlaxoSmithKline Biologicals) and W/O emulsion (e.g. ISA51 and ISA720 from Seppic, or as disclosed in WO 2008/009309). For example, a suitable adjuvant emulsion for the process according to the present invention is that disclosed in WO 2007/006939;

2) a natural extracts such as: the saponin extract QS21 and its semi-synthetic derivatives such as those developed by Avantogen, bacterial cell wall extracts (e.g. micobacterium cell wall skeleton developed by Corixa/GS and micobaterium cord factor and its synthetic derivative, trehalose dimycholate);

3) a stimulator of Toll Like Receptors (TLR). It is particular natural or synthetic TLR agonists (e.g. synthetic lipopeptides that stimulate TLR2/1 or TLR2/6 heterodimers, double stranded RNA that stimulates TLR3, LPS and its derivative MPL that stimulate TLR4, E6020 and RC-529 that stimulate TLR4, flagellin that stimulates TLR5, single stranded RNA and 3M's synthetic imidazoquinolines that stimulate TLR7 and/or TLR8, CpG DNA that stimulates TLR9, natural or synthetic NOD agonists (e.g. Muramyl dipeptides), natural or synthetic RIG agonists (e.g. viral nucleic acids and in particular 3' phosphate RNA).

When there is no incompatibility between the adjuvant and the liquid bulk solution of antigen(s) it can be added directly to the solution. The liquid bulk solution of antigen(s) and adjuvant may be for instance a liquid bulk solution of an anatoxin adsorbed on an aluminium salt (alun, aluminium phosphate, aluminium hydroxide) containing a stabilizer such as mannose, an oligosaccharide such as sucrose, lactose, trehalose, maltose, a sugar alcohol such as sorbitol, mannitol or inositol, or a mixture thereof. Examples of such compositions are described in particular in WO 2009/109550, the subject-matter of which is incorporated by reference. The freeze-dried particles of the non adjuvanted or adjuvanted vaccine composition are usually under the form of spheric particles having a mean diameter between 200 μm and 1500 μm. Furthermore, the freeze-dried particles of the vaccine compositions obtained are sterile.

While the current invention has been described in relation to its preferred embodiment, it is to be understood that this description is for illustrative purposes only. Accordingly, it is intended that the invention be limited only by the scope of the claims appended hereto.

This application claims priority of European patent application EP 14 002 529.7-1351, the subject-matters of which are listed below for the sake of completeness:

Item 1. Liquid feeding device for the generation of droplets, in particular for the use in a process line for the production of freeze-dried particles, with a droplet ejection section for ejecting liquid droplets in an ejection direction, the droplet ejection section comprising at least one inlet port for receiving a liquid to be ejected, a liquid chamber for retaining the liquid, and a nozzle for ejecting the liquid from the liquid chamber to form droplets, wherein the liquid chamber is restricted by a membrane on one side thereof, the membrane being vibratable by an excitation unit, wherein the longitudinal axis of the liquid chamber is tilted relative to the longitudinal axis of the nozzle, and/or the liquid feeding device further comprises a deflection section for separating the droplets from each other by means of a gas jet.

Item 2. Liquid feeding device according to item 1, wherein the deflection section gas jet intersects with an ejection path of the liquid ejected from the liquid chamber.

Item 3. Liquid feeding device according to item 1 or 2, wherein the deflection section comprises at least one deflection tube for emitting the gas jet, the at least one deflection tube protruding from a main body of the deflection section in the ejection direction of the liquid.

Item 4. Liquid feeding device according to item 3, wherein the deflection section comprises two deflection tubes arranged opposite to each other, and wherein the emitted gas jets meet each other at an ejection path of the liquid ejected from the liquid chamber, intersecting with the same.

Item 5. Liquid feeding device according to item 3 or 4, wherein each deflection tube comprises at least two gas jet outlet ports, and wherein the gas jet outlet port at the tip of the respective deflection tube connects with the tube interior at its edge, preferably wherein each deflection tube comprises three gas jet outlet ports.

Item 6. Liquid feeding device according to any one of the preceding items, wherein the droplets pass through a recess provided in a main body of the deflection section, preferably wherein the recess is a central through-hole extending through the main body of the deflection section.

Item 7. Liquid feeding device according to any one of the preceding items, wherein the droplet ejection section further comprises at least one outlet port, preferably wherein the at least one outlet port is arranged at an outer circumference of the liquid chamber.

Item 8. Liquid feeding device according item 7, wherein the longitudinal axis of the liquid chamber is tilted relative to the longitudinal axis of the nozzle in a way that the at least one outlet port is provided at the highest level of the liquid chamber.

Item 9. Liquid feeding device according item 7 or 8, wherein the at least one outlet port serves for drainage of excessive liquid to be ejected from the liquid chamber and/or serves for discharge of SiP fluid and/or CiP fluid introduced through the at least one inlet port of the droplet ejection section.

Item 10. Liquid feeding device according to any one of the preceding items, wherein the excitation unit comprises a combination of a permanent magnet separably attachable to the membrane opposite the liquid chamber and an electromagnetic coil for actuating the permanent magnet, preferably wherein a damping element is provided around the permanent magnet, more preferably also between the permanent magnet and the electromagnetic coil, further preferably wherein the damping element is made out of silicone.

Item 11. Liquid feeding device according to any one of the preceding items, wherein the membrane is a stainless steel membrane.

Item 12. Liquid feeding device according to any one of the preceding items, wherein the droplet ejection section comprises an actuation portion and a nozzle portion, the actuation portion comprising at least the excitation unit, and the nozzle portion comprising at least the at least one inlet port, the liquid chamber, the nozzle and the membrane.

Item 13. Liquid feeding device according to item 12, wherein the nozzle portion comprises a nozzle portion main body and a nozzle body provided separately from the nozzle portion main body, preferably wherein the nozzle body is permanently installed in a central through-hole in the nozzle portion main body, more preferably by laser welding.

Item 14. Liquid feeding device according to item 12 or 13, wherein the membrane is welded to the nozzle portion for airtightly closing the liquid chamber on one side, preferably by laser welding.

Item 15. Liquid feeding device according to any one of the preceding items, further comprising a CiP/SiP section arranged between the droplet ejection section and the deflection section, for providing CiP fluid and/or SiP fluid to the parts of the liquid feeding device subsequent to the droplet ejection section.

Item 16. Liquid feeding device according to any one of the preceding items, further comprising a droplet counting section for counting the droplets, preferably provided before the deflection section in the ejection direction of the liquid.

Item 17. Freezing chamber of a process line for the production of freeze-dried particles, preferably for the pharmaceutical field, comprising a liquid feeding device according to any one of the preceding items, for the generation of droplets to be fed into the freezing chamber.

Item 18. Process line for the production of freeze-dried particles, comprising a freezing chamber according to item 17.

Item 19. A process for preparing a vaccine composition comprising one or more antigens in the form of freeze-dried particles comprising at least a step of generating liquid droplets of said vaccine composition with a liquid feeding device according to anyone of items 1 to 16.

Item 20. A process for preparing an adjuvant containing vaccine composition comprising one or more antigens in the form of freeze-dried particles comprising:
- at least a step of generating liquid droplets of said vaccine composition with a liquid feeding device according to anyone of items 1 to 16, or
- at least the steps of generating liquid droplets of an antigen(s)-containing composition with a liquid feeding device according to anyone of items 1 to 16, of generating liquid droplets of an adjuvant-containing composition with a liquid feeding device according to anyone of items 1 to 16, freeze-drying the droplets to obtain freeze-dried particles, and blending the freeze-dried particles of antigen(s) with the freeze-dried particles of adjuvant.

Item 21. A process according to item 19 or 20, wherein all the steps are carried out under sterile conditions.

Item 22. A process according to items 19 or 21, wherein the freeze-dried particles are sterile.

What is claimed is:

1. Liquid feeding device for the generation of droplets, comprising:
    a droplet ejection section for ejecting liquid droplets in a droplets ejection path, the liquid droplets being generated by an excitation unit from a liquid to be ejected, the droplet ejection section comprising:
    at least one inlet port for receiving the liquid,
    a liquid chamber for retaining the liquid,
    a nozzle for ejecting the liquid from the liquid chamber to form the liquid droplets, and
    at least one outlet port for drainage of excessive liquid from the liquid chamber, said at least one outlet port is arranged at an outer circumference of the liquid chamber,
    wherein the liquid chamber is restricted by a membrane on one side thereof, the membrane is vibrated by the excitation unit; and
    a deflection section for separating the liquid droplets from each other by at least one gas jet,
    wherein the deflection section gas jet intersects perpendicular with the droplets ejection path.

2. Liquid feeding device according to claim 1, wherein the longitudinal axis of the liquid chamber is tilted relative to the longitudinal axis of the nozzle.

3. Liquid feeding device according to claim 1, wherein the deflection section comprises at least one deflection tube for emitting the gas jet, the at least one deflection tube protruding from a main body of the deflection section in the ejection direction of the liquid.

4. Liquid feeding device according to claim 3, wherein the deflection section comprises at least two deflection tubes arranged opposite to each other, and wherein the emitted gas jets meet each other at an ejection path of the liquid ejected from the liquid chamber, intersecting with the same.

5. Liquid feeding device according to claim 4, wherein the deflection section comprises four deflection tubes, and wherein the emitted gas jets meet each other at an ejection path of the liquid ejected from the liquid chamber, intersecting with the same.

6. Liquid feeding device according to claim 3, wherein each deflection tube comprises at least two gas jet outlet ports, and wherein the gas jet outlet port at the tip of the respective deflection tube connects with the tube interior at its edge.

7. Liquid feeding device according to claim 1, wherein the droplets pass through a recess provided in a main body of the deflection section.

8. Liquid feeding device according to claim 1, wherein the longitudinal axis of the liquid chamber is tilted relative to the longitudinal axis of the nozzle in a way that the at least one outlet port is provided at the highest level of the liquid chamber.

9. Liquid feeding device according to claim 1, wherein the at least one outlet port serves for discharge of SiP fluid and/or CiP fluid introduced through the at least one inlet port of the droplet ejection section.

10. Liquid feeding device according to claim 1, wherein the excitation unit comprises a combination of a permanent magnet separably attachable to the membrane opposite the liquid chamber and an electromagnetic coil for actuating the permanent magnet.

11. Liquid feeding device according to claim 1, wherein the membrane is a stainless steel membrane.

12. Liquid feeding device according to claim 1, wherein the droplet ejection section comprises an actuation portion and a nozzle portion, the actuation portion comprising at least the excitation unit, and the nozzle portion comprising at least the at least one inlet port, the liquid chamber, the nozzle and the membrane.

13. Liquid feeding device according to claim 12, wherein the nozzle portion comprises a nozzle portion main body and a nozzle body provided separately from the nozzle portion main body.

14. Liquid feeding device according to claim 12, wherein the membrane is welded to the nozzle portion for air tightly closing the liquid chamber on one side.

15. Liquid feeding device according to claim 1, further comprising a CiP/SiP section arranged between the droplet ejection section and the deflection section, for providing CiP fluid and/or SiP fluid to the parts of the liquid feeding device subsequent to the droplet ejection section.

16. Liquid feeding device according to claim 1, further comprising a droplet counting section for counting the droplets.

17. Process line for the production of freeze-dried particles, comprising
a liquid feeding device according to claim 1, for the generation of droplets,
a freezing chamber for freeze-congealing droplets fed from the liquid feeding device, and
a freeze-dryer for lyophilization of the frozen droplets.

18. A process for preparing a vaccine composition comprising one or more antigens in the form of freeze-dried particles comprising at least a step of generating liquid droplets of said vaccine composition with a liquid feeding device according to claim 1.

19. The process according to claim 18, wherein all the steps are carried out under sterile conditions.

20. The process according to claim 18, wherein the freeze-dried particles are sterile.

21. A process for preparing an adjuvant containing vaccine composition comprising one or more antigens in the form of freeze-dried particles comprising:
at least a step of generating liquid droplets of said vaccine composition with the liquid feeding device according to claim 1, or
at least the steps of generating liquid droplets of an antigen(s)-containing composition with the liquid feeding device according to claim 1, of generating liquid droplets of an adjuvant-containing composition with the liquid feeding device according to claim 1, freeze-drying the droplets to obtain freeze-dried particles, and blending the freeze-dried particles of antigen(s) with the freeze-dried particles of adjuvant.

22. A process for manufacturing freeze-dried particles, the process comprising at least a step of generating liquid droplets with a liquid feeding device according to claim 1.

23. Liquid feeding device for the generation of droplets, comprising:
a droplet ejection section for ejecting liquid droplets in a droplets ejection path, the liquid droplets being generated by an excitation unit from a liquid to be ejected, the droplet ejection section comprising:
at least one inlet port for receiving the liquid to be ejected,
a liquid chamber for retaining the liquid,
a nozzle for ejecting the liquid from the liquid chamber to form the liquid droplets, and
at least one outlet port for drainage of excessive liquid from the liquid chamber, said at least one outlet port is arranged at an outer circumference of the liquid chamber,
wherein the liquid chamber is restricted by a membrane on one side thereof, the membrane is vibrated by the excitation unit, and
wherein the longitudinal axis of the liquid chamber is tilted relative to the longitudinal axis of the nozzle.

24. Liquid feeding device according to claim 23, further comprising a deflection section for separating the liquid droplets from each other by at least one gas jet, wherein the deflection section gas jet intersects perpendicular with an ejection path of the liquid ejected from the liquid chamber.

25. Liquid feeding device according to claim 24, wherein the deflection section comprises at least one deflection tube for emitting the gas jet, the at least one deflection tube protruding from a main body of the deflection section in the droplets ejection path.

26. Liquid feeding device according to claim 25, wherein the deflection section comprises at least two deflection tubes arranged opposite to each other, and wherein the emitted gas jets meet each other at an ejection path of the liquid ejected from the liquid chamber, intersecting with the same.

27. Liquid feeding device according to claim 26, wherein the deflection section comprises four deflection tubes, and wherein the emitted gas jets meet each other at an ejection path of the liquid ejected from the liquid chamber, intersecting with the same.

28. Liquid feeding device according to claim 25, wherein each deflection tube comprises at least two gas jet outlet ports, and wherein the gas jet outlet port at the tip of the respective deflection tube connects with the tube interior at its edge.

29. Liquid feeding device according to claim 24, wherein the droplets pass through a recess provided in a main body of the deflection section.

30. Liquid feeding device according to claim 24, wherein the longitudinal axis of the liquid chamber is tilted relative to the longitudinal axis of the nozzle in a way that the at least one outlet port is provided at the highest level of the liquid chamber.

31. Liquid feeding device according to claim 24, wherein the at least one outlet port serves for discharge of SiP fluid and/or CiP fluid introduced through the at least one inlet port of the droplet ejection section.

32. Liquid feeding device according to claim 24, wherein the excitation unit comprises a combination of a permanent magnet separably attachable to the membrane opposite the liquid chamber and an electromagnetic coil for actuating the permanent magnet.

33. Liquid feeding device according to claim 24, wherein the membrane is a stainless steel membrane.

34. Liquid feeding device according to claim 24, wherein the droplet ejection section comprises an actuation portion and a nozzle portion, the actuation portion comprising at least the excitation unit, and the nozzle portion comprising at least the at least one inlet port, the liquid chamber, the nozzle and the membrane.

35. Liquid feeding device according to claim 34, wherein the nozzle portion comprises a nozzle portion main body and a nozzle body provided separately from the nozzle portion main body.

36. Liquid feeding device according to claim 35, wherein the membrane is welded to the nozzle portion for air tightly closing the liquid chamber on one side.

37. Liquid feeding device according to claim 36, further comprising a CiP/SiP section arranged between the droplet ejection section and the deflection section, for providing CiP fluid and/or SiP fluid to the parts of the liquid feeding device subsequent to the droplet ejection section.

38. Liquid feeding device according to claim 24, further comprising a droplet counting section for counting the droplets.

39. Liquid feeding device for the generation of droplets, comprising:
   a droplet ejection section for ejecting liquid droplets in a droplets ejection path, the liquid droplets being generated by an excitation unit from a liquid to be ejected, the droplet ejection section comprising:
   at least one inlet port for receiving the liquid,
   a liquid chamber for retaining the liquid,
   a nozzle for ejecting the liquid from the liquid chamber to form the liquid droplets, and
   at least one outlet port,
   wherein the liquid chamber is restricted by a membrane on one side thereof, the membrane is vibrated by the excitation unit; and
   a deflection section for separating the liquid droplets from each other by at least two gas jets, said deflection section comprises at least two deflection tubes arranged opposite to each other, for emitting the at least two gas jets,
   wherein the deflection section gas jet intersects perpendicular with the droplets ejection path, and
   wherein the emitted gas jets meet each other at an ejection path of the liquid ejected from the liquid chamber, intersecting with the same.

40. Liquid feeding device for the generation of droplets, comprising:
   a droplet ejection section for ejecting liquid droplets in a droplets ejection path, the liquid droplets being generated by an excitation unit from a liquid to be ejected, the droplet ejection section comprising:
   at least one inlet port for receiving the liquid,
   a liquid chamber for retaining the liquid,
   a nozzle for ejecting the liquid from the liquid chamber to form the liquid droplets, and
   at least one outlet port,
   wherein the liquid chamber is restricted by a membrane on one side thereof, the membrane is vibrated by the excitation unit;
   a deflection section for separating the liquid droplets from each other by at least one gas jet,
   wherein the deflection section gas jet intersects perpendicular with the droplets ejection path; and
   a CiP/SiP section arranged between the droplet ejection section and the deflection section, for providing CiP fluid and/or SiP fluid to the parts of the liquid feeding device subsequent to the droplet ejection section.

\* \* \* \* \*